United States Patent
Imran

(10) Patent No.: US 12,128,133 B2
(45) Date of Patent: Oct. 29, 2024

(54) INGESTIBLE DEVICE WITH EXPANDABLE ENCLOSURE

(71) Applicant: RANI THERAPEUTICS, LLC, San Jose, CA (US)

(72) Inventor: Mir A. Imran, Los Altos Hills, CA (US)

(73) Assignee: RANI THERAPEUTICS, LLC, San Jose, CA (US)

( * ) Notice: Subject to any disclaimer, the term of this patent is extended or adjusted under 35 U.S.C. 154(b) by 388 days.

(21) Appl. No.: 16/579,112

(22) Filed: Sep. 23, 2019

(65) Prior Publication Data

US 2020/0093740 A1  Mar. 26, 2020

Related U.S. Application Data

(60) Provisional application No. 62/736,263, filed on Sep. 25, 2018.

(51) Int. Cl.
| | |
|---|---|
| *A61K 9/00* | (2006.01) |
| *A61M 25/10* | (2013.01) |
| *C07K 16/24* | (2006.01) |
| *C07K 16/28* | (2006.01) |

(52) U.S. Cl.
CPC ........... *A61K 9/0065* (2013.01); *A61M 25/10* (2013.01); *C07K 16/241* (2013.01); *C07K 16/244* (2013.01); *C07K 16/283* (2013.01); *A61M 2025/105* (2013.01)

(58) Field of Classification Search
CPC ............... A61K 9/0065; A61M 25/10; A61M 2025/105; C07K 16/241; C07K 16/244; C07K 16/283
USPC ........................................................ 424/435
See application file for complete search history.

(56) References Cited

U.S. PATENT DOCUMENTS

| | | |
|---|---|---|
| 2005/0058701 A1 | 3/2005 | Gross et al. |
| 2008/0188837 A1 | 8/2008 | Belsky et al. |
| 2008/0275430 A1 | 11/2008 | Belsky et al. |
| 2010/0021536 A1 | 1/2010 | Gross |
| 2012/0059257 A1 | 3/2012 | Duck et al. |
| 2016/0213234 A1 | 7/2016 | Poon et al. |
| 2017/0050005 A1 | 2/2017 | Imran |
| 2017/0172778 A1 | 6/2017 | Brister et al. |

FOREIGN PATENT DOCUMENTS

| | | |
|---|---|---|
| CN | 1802181 | 7/2006 |
| CN | 104023740 A | 9/2014 |
| CN | 105263461 | 1/2016 |
| CN | 105877685 | 8/2016 |
| CN | 108401419 A | 8/2018 |
| WO | WO-2004/084763 A2 | 10/2004 |
| WO | WO 2006/0020929 | 2/2006 |
| WO | WO-2006/020929 A2 | 2/2006 |
| WO | WO-2013/003824 A1 | 1/2013 |
| WO | WO-2014/159604 A1 | 10/2014 |
| WO | WO-2017/044665 A1 | 3/2017 |

OTHER PUBLICATIONS

ISR and Written Opinion in PCT/US2019/052718 dated Jan. 9, 2020.

*Primary Examiner* — Adam C Milligan

(74) *Attorney, Agent, or Firm* — Foley & Lardner LLP

(57) ABSTRACT

An embodiment of an ingestible device for the delivery of a therapeutic agent includes a swallowable outer shell and a delivery mechanism within the outer shell. The delivery mechanism includes an expandable enclosure. The delivery mechanism is triggerable in situ within a gastrointestinal (GI) tract of a body to expand multiple regions of the expandable enclosure to an expanded state at a delivery location within the body. The multiple regions include a head region and a tail region with a protective recess defined between the head region and the tail region, and a retention region within the protective recess. A dimension of the retention region as expanded is less than a dimension of the head region as expanded and less than a dimension of the tail region as expanded. The ingestible device includes a shaped composition disposed at the retention region.

21 Claims, 17 Drawing Sheets

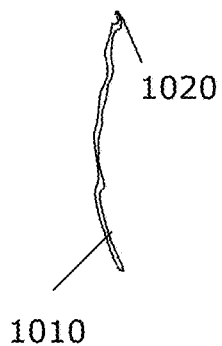
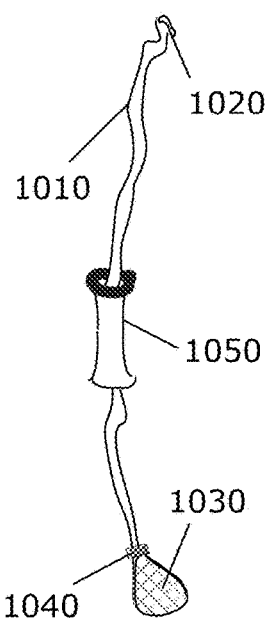
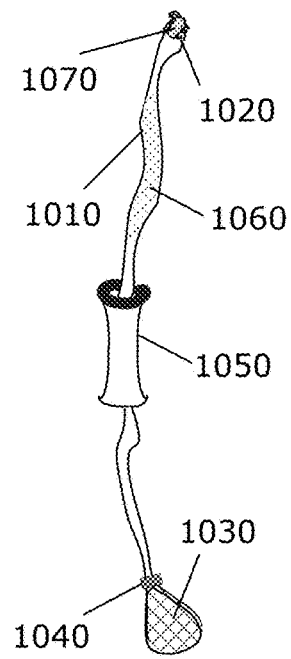
FIG. 10A  FIG. 10B  FIG. 10C
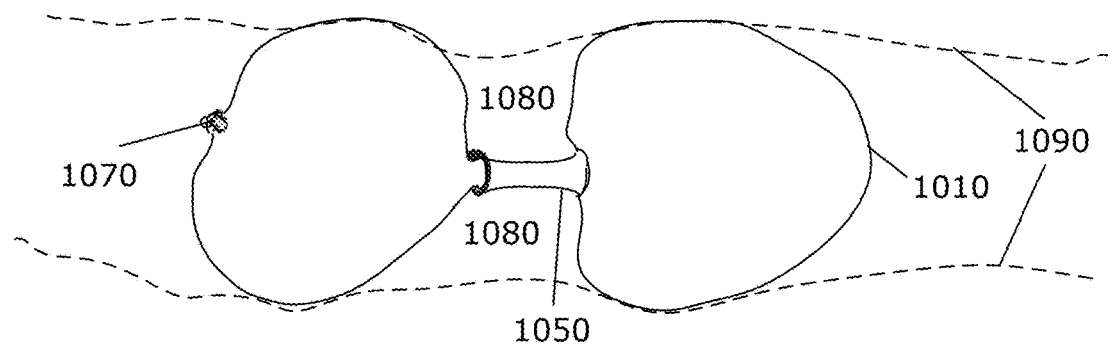
FIG. 10D
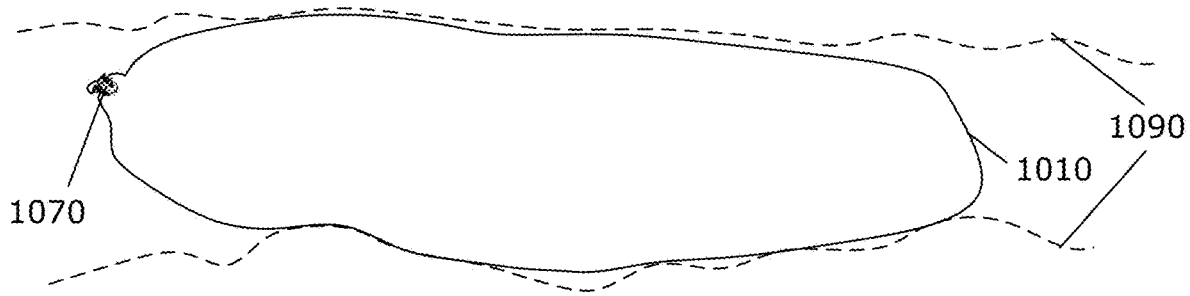
FIG. 10E In accordance with a therapeutic regimen, ingesting an ingestible device, the ingestible device including a delivery mechanism including an expandable enclosure, and the ingestible device further including a shaped composition including a therapeutic agent and a delivery enhancing agent

1400

Provide for expansion a head region and a tail region of the expandable enclosure, the shaped composition being positioned adjacent to a retention region in a protective recess formed between the head region and the tail region

1410

Provide for exposure of the delivery enhancing agent to the gastrointestinal tract, to enhance transport of the therapeutic agent at a delivery location of the gastrointestinal tract

1420

Provide for exposure of the therapeutic agent to the gastrointestinal tract at the target delivery location, to allow transport of the therapeutic agent across an interior wall of the gastrointestinal tract at the delivery location

INGESTIBLE DEVICE WITH EXPANDABLE ENCLOSURE

CROSS-REFERENCE TO RELATED APPLICATIONS

This application claims the benefit of and the priority to U.S. Provisional Patent Application Ser. No. 62/736,263 titled "Ingestible Device with Expandable Enclosure" filed Sep. 25, 2018, the contents of which are incorporated herein in their entirety for all purposes.

BACKGROUND

Advances in medicine have identified numerous chronic diseases, such as psoriasis, Crohn's disease, rheumatoid arthritis, diabetes, and hemophilia, to name a few. Many therapeutics used to treat chronic diseases are delivered primarily or exclusively by way of injections which can be painful and inconvenient, and thus compliance with a treatment program including the injections may not be as good as would be compliance with an oral delivery regimen if it were available. However, many historical approaches to oral delivery of injectable therapeutics have not been successful. New approaches to oral delivery of therapeutics previously delivered in injectable form would thus be desirable.

SUMMARY

Embodiments provide ingestible devices and associated methods for the oral delivery of formulations (e.g., one or more therapeutic agents and/or other compounds). In many embodiments, an expandable enclosure (e.g., a balloon) expands in situ to deliver one or more formulations at a delivery location in the gastrointestinal (GI) tract. The expandable enclosure is structured such that, when inflated, portions of the expandable enclosure form one or more protective recesses. When inflated within the GI tract, a protective recess may be bounded by the GI tract to form a protective volume, so that formulations disposed within the protective recess are exposed to the GI tract within the protective volume. Prior to expansion, the expandable enclosure is included as part of a delivery device within an outer shell of an ingestible device. In one or more embodiments, the ingestible device is structured to be swallowed and to travel through the GI tract to a target delivery location.

BRIEF DESCRIPTION OF THE DRAWINGS

FIG. 10A, FIG. 10B, FIG. 10C, FIG. 10D, and FIG. 10E illustrate a prototype of an embodiment of an ingestible device.

FIG. 14 illustrates an embodiment of a method for oral delivery of an ingestible device including a therapeutic formulation.

Figure 1A:
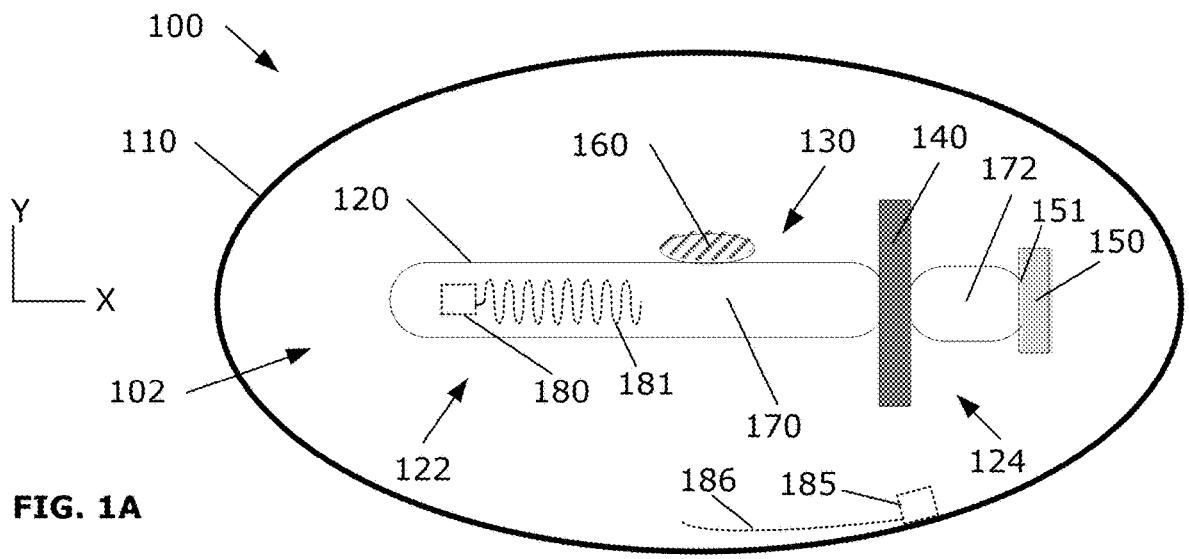
FIG. 1A, FIG. 1B, FIG. 1C, FIG. 1D, FIG. 1E, and FIG. 1F illustrate embodiments of an ingestible device depicted during a progression through a gastrointestinal tract to a delivery location within a body.

These and other embodiments are described below in conjunction with the figures of the present disclosure by way of example and not limitation. Other embodiments that will become apparent from the figures and descriptions are encompassed by the present disclosure. Further, a combination of features from different embodiments are encompassed by the present disclosure.

For convenience of description, an X-Y plane is indicated in multiple ones of the figures herein by an X-axis perpendicular to a Y-axis. In addition, a Z-axis perpendicular to the X-plane (illustrated with respect to cross-sectional views) in combination with the X-Y plane defines a three-dimensional X-Y-Z space.

Relative placement and relative size of the representations of components in any of the illustrations are not intended to indicate or limit relative placement or relative size of actual components.

DETAILED DESCRIPTION

When used in the present disclosure, the term "e.g." or the term "such as" indicates that a list of one or more non-limiting example(s) follows; it is to be understood that other examples not listed are also within the scope of the present disclosure.

The terms "degrade", "degrading", "degraded", and "degradation" refer herein to weakening, partially degrading, or fully degrading, such as by dissolution, chemical degradation, decomposition, chemical modification, mechanical degradation, or disintegration.

The terms "design", "designing", and "designed" refer herein to characteristics intentionally incorporated into a design based on estimates of tolerances related to the design (e.g., component tolerances and/or manufacturing tolerances) and estimates of environmental conditions expected to be encountered by the design (e.g., temperature, humidity, external or internal ambient pressure, external or internal mechanical pressure or stress, age of product, physiology, body chemistry, biological composition and/or chemical compositions of fluids and tissue, pH, species, diet, health, gender, age, ancestry, disease, tissue damage, or the combination of such); it is to be understood that actual tolerances and environmental conditions before and/or after ingestion may affect such designed characteristics so that different ingestible devices with a same design can have different actual values with respect to those designed characteristics. Use of the terms "design", "designing", and "designed" herein encompass also variations or modifications to the design, a component structured (defined below) in accordance with the design, and design modifications implemented on a component after it is manufactured (defined below).

The term "digestive matter" refers herein to biological matter such as blood, tissue, fluid, enzymes, and other secretions of the body along the GI tract, and also includes other matter (e.g., food in an undigested or a digested form) traversing the GI tract.

The term "fluid" refers herein to a gas or a liquid, or a combination thereof.

The terms "ingest", "ingesting", and "ingested" refer herein to taking into the stomach, whether by swallowing or by other means of depositing into the stomach (e.g., by depositing into the stomach by endoscope or depositing into the stomach via a port).

The terms "manufacture", "manufacturing", and "manufactured" as related to a component refer herein to making the component, whether made wholly or in part by hand or made wholly or in part in an automated fashion.

The term "structured" refers herein to a component or system that is manufactured according to a concept or design or variations thereof or modifications thereto (whether such variations or modifications occur before, during, or after manufacture) whether or not such concept or design is captured in a writing.

With advances in biotechnology, a wide variety of biologically derived therapeutic agents (herein referred to as biologics) have been developed which allow for the improved treatment of a variety of high prevalence chronic diseases such as diabetes and other glucose regulation disorders, multiple sclerosis, psoriasis and other autoimmune diseases, eosinophil-related diseases, and hemophilia and other clotting diseases. Such biologics include antibodies, insulin, Factor VIII, and anti-eosinophil antibodies, to name just a few. Due to the large size and/or delicate structure of these biologics, they have not been able to be delivered orally. The molecules may be poorly absorbed, or may be broken down in the GI tract before absorption. As such, administration of biologics has heretofore required parenteral injection (e.g., intramuscular, subdermal or intravenous injection). However, these injections are painful, inconvenient (often requiring trips to a medical facility), and not without risk, including tissue site reactions and infection. Accordingly, compliance with a treatment program involving injections may not be as good as would be compliance with an oral delivery regimen if it were available. While many attempts have been made towards the oral delivery of biologics and related compounds, such attempts have largely been unsuccessful due to the breakdown of the molecules in the GI tract and/or poor or unpredictable absorption and resulting low bioavailability. Thus, there is a need for new approaches for the oral delivery of biologics and other therapeutic agents which previously could only be delivered by parenteral injection.

As discussed in detail below, embodiments provide for an ingestible device for delivering therapeutic formulations within a GI tract of a body (e.g., mammalian body, such as a human body). According to embodiments, the ingestible device includes an outer shell and a delivery mechanism disposed in a space defined within the outer shell. The delivery mechanism includes an expandable enclosure. The outer shell degrades in situ (e.g., at or near a target delivery location), exposing the delivery mechanism to digestive matter. The delivery mechanism is triggerable with exposure to the digestive matter to expand multiple regions of the expandable enclosure to an expanded state. The multiple regions can include a head region, a tail region, and a retention region. A dimension of the retention region as expanded is less than a dimension of the head region as expanded and less than a dimension of the tail region as expanded, such that the head region and the tail region together define a protective recess in which the retention region is located. In situ, the head region and/or the tail region expand against a wall of the GI tract, and the protective recess is bounded in situ by the head region, the tail region, and the wall, forming a partially or fully sealed section of the GI tract to minimize or avoid digestive matter entering the protective recess. One or more shaped compositions can be disposed in the retention region so as to be exposed to the GI tract within the protective recess.

FIGS. 1A-1F illustrate an embodiment of an ingestible device 100 as it progresses through various states or stages during traversal through the GI tract (e.g., to a target delivery location within a body).

In FIG. 1A, the ingestible device 100 includes an outer shell 110 and a delivery mechanism 102. The outer shell 110 encases (e.g., encapsulates, surrounds, or covers) the delivery mechanism 102. In FIG. 1A, the outer shell 110 is shown in cross-section along a length of the ingestible device 100 to expose the delivery mechanism 102.

In one or more embodiments, the outer shell 110 can include one or more layers with material compositions that are reactive to different expected characteristics of digestive matter along different portions of the GI tract, such that the outer shell 110 can survive traversal through a portion of the GI tract after ingestion while maintaining a fluid barrier against digestive matter entering the ingestible device 100, and then the fluid barrier is compromised at a delivery location (e.g., at or near a target delivery location). For example, the outer shell 110 can be structured to provide a fluid barrier for an expected duration that the outer shell 110 will reside in a stomach. For another example, the outer shell 110 can be structured to withstand degradation at pH values associated with a lower stomach area where the ingestible device 100 is expected to be detained for a time (e.g., the outer shell 110 structure includes an enteric coating that withstands degradation at pH values in a range of 1.5-3.5) and then degrade at pH values associated with the small intestine (e.g., pH>7).

In one or more embodiments, a layer of the outer shell 110 is a capsule, the delivery mechanism 102 is disposed inside the capsule, and the outer shell 110 optionally further includes one or more layers over the capsule.

In one or more embodiments, the ingestible device 100 does not include a capsule. For example, the outer shell 110 can be disposed directly on the delivery mechanism 102, such as by spraying or dripping a material onto the delivery mechanism 102 to form a layer or layers of the outer shell 110, or dipping the delivery mechanism 102 into a material to form a layer or layers of the outer shell 110. An embodiment of the outer shell 110 is illustrated and described below with respect to FIG. 2.

Referring still to FIG. 1A, the delivery mechanism 102 can include an expandable enclosure 120 having a head region 122, a tail region 124, and a retention region 130. The nomenclature "head" and "tail" are used for convenience of explanation and do not necessarily denote orientation of the ingestible device 100 during traversal of the ingestible device 100 through the GI tract.

The delivery mechanism 102 can be divided into multiple sections. In the illustration of FIG. 1A, a separation barrier 140 as engaged divides the expandable enclosure 120 into a volume section 170 and a volume section 172. The separation barrier 140 can correspond to any structure that engages to close off the expandable enclosure 120. In one or more embodiments, the volume section 170 contains a first chemical reactant and the volume section 172 contains a second chemical reactant; the separation barrier 140 minimizes or prevents mixing of the first chemical reactant and the second chemical reactant while the separation barrier 140 is engaged, and when the separation barrier 140 disengages (e.g., as a result of degradation), the first chemical reactant and the second chemical reactant mix to cause a desired expansion effect. For example, disengagement of the separation barrier 140 can allow potassium bicarbonate and citric acid to mix and form a gas and thereby cause a desired expansion effect. Although the delivery mechanism 102 is illustrated in FIG. 1A as including one separation barrier 140, there may be multiple separation barriers including the separation barrier 140 dividing the expandable enclosure 120 into multiple volume sections 170, 172 and one or more other volume sections.

The delivery mechanism 102 can include one or more mechanisms to close off (e.g., clamp down on, plug, or otherwise seal) an opening in the expandable enclosure 120 and thereby provide a fluid barrier between an interior of the expandable enclosure 120 and an exterior of the expandable enclosure 120. In the illustration of FIGS. 1A-1E, a seal 150 closes off an opening of the expandable enclosure 120 in the tail region 124. Prior to engaging the seal 150, an opening 151 in the expandable enclosure 120 can provide access to an interior region of the expandable enclosure 120 so that, during assembly of the delivery mechanism 102, the expandable enclosure 120 can accept an expansion mechanism (e.g., the first and second chemical reactants that when mixed cause the desired expansion effect of the expandable enclosure 120). The seal 150 after engagement then retains the contents of the expandable enclosure 120 (e.g., contents of the volume section 172). After ingestion, the seal 150 can be structured to disengage (e.g., by degrading) at a target delivery location to allow the contents of the expandable enclosure 120 (e.g., a gas) to escape through the opening 151.

Although the seal 150 is illustrated as closing off the opening 151 at an end of the expandable enclosure 120 for convenience of illustration, it is to be understood that an opening can be structured on any part of the expandable enclosure 120 and closed off by a mechanism such as the seal 150, and multiple openings may each be closed off by a seal such as the seal 150.

Design engagement time of the separation barrier 140 and the seal 150 can be achieved by structure. Engagement time herein refers to a period of time in which the respective separation barrier 140 or seal 150 remains engaged and maintaining the respective barrier or seal after exposure to conditions at the delivery location. Design engagement time is the expected engagement time at a target delivery location. Designing for engagement time includes design of structural aspects and selection of material(s). For example, a designed engagement time can be adjusted by changing design dimensions of a structure and/or by changing relative dimensions of portions of the structure with respect to each other. For another example, a designed engagement time can be adjusted by changing a thickness of a material, by selecting a different material, and/or by using a different combination of materials. One or more of the materials can be selected based on known or predicted degradation properties when exposed to environmental conditions expected at the target delivery location.

In one or more embodiments, the seal 150 is structured for longer engagement time at a target delivery location than the engagement time of the separation barrier 140. For example, the engagement time of the separation barrier 140 may be less than or equal to five minutes (e.g., approximately one minute, in a range of one to five minutes, greater than five seconds, and so forth), and the engagement time of the seal 150 may be less than or equal to thirty minutes (e.g., greater than five minutes, in a range of one minute to ten minutes, greater than one minute, in a range of ten to twenty minutes, and so forth).

The ingestible device 100 can include one or more shaped compositions positioned at one or more retention regions. A single shaped composition 160 at the single retention region 130 is illustrated in FIGS. 1A-1D for convenience of discussion; it is to be understood that a reference to the shaped composition 160 applies to each of multiple shaped compositions 160 of an embodiment unless otherwise specified.

The shaped composition 160 can be affixed to the expandable enclosure 120 to maintain positioning of the shaped composition 160 at the retention region 130. In one or more embodiments, the shaped composition 160 is affixed to the expandable enclosure 120 using a material including one or more of sugar, maltose, polylactic acid (PLA), polyethylene oxide (PEO), or other biodegradable material. In one or more embodiments, the shaped composition 160 is affixed to the expandable enclosure 120 using a non-biodegradable material.

The shaped composition 160 can include multiple layers. As described in more detail below, in one or more embodiments, the shaped composition 160 can include a layer or layers to withstand premature degradation (e.g., before an intended degradation at the target delivery location).

A discussion will now be provided regarding therapeutic formulations which may be delivered by one or more embodiments of the ingestible device 100. A therapeutic formulation can include one or more therapeutic agents, and the shaped composition 160 can include one or more therapeutic formulations. A therapeutic agent may confer a therapeutic or other biological benefit to a body when released at the delivery location. A therapeutic agent can be any of various substances, such as a pharmacologically active agent for treating a disease or other condition of a body, a vaccine, a cell (e.g., produced by or from living organisms or contain components of living organisms), a vitamin, a mineral or another nutritional or herbal supplement, or DNA or SiRNA transcripts (e.g., for modifying genetic abnormalities, conditions, or disorders).

Examples of pharmacologically active agents include without limitation peptides, proteins, immunoglobulins (e.g., antibodies), large molecules, small molecules, hormones, and biologically active variants and derivatives of any of the foregoing.

A therapeutic agent can be in a class of antibodies, such as immunoglobulin G (e.g., a TNF-alpha antibody such as adalimumab, an interleukin in the IL-17 family of interleukins such as brodalumab, secukinumab, or ixekizumab), an anti-eosinophil antibody, or any other class, and may be humanized or not.

Examples of vitamins, minerals, or other nutritional or herbal supplements include without limitation vitamin A, thiamin, niacin, riboflavin, vitamin B-6, vitamin B-12, other B-vitamins, vitamin C (ascorbic acid), vitamin D, vitamin E, folic acid, phosphorous, iron, calcium, and magnesium.

Examples of cells include without limitation stem cells, red blood cells, white blood cells, neurons, and other viable cells.

Examples of vaccines include without limitation vaccines against various bacteria and viruses or proteins thereof (e.g., influenza, meningitis, human papillomavirus (HPV), or chicken pox). In various embodiments of vaccines to viruses, the vaccine can correspond to various attenuated viruses.

The therapeutic formulation can also include one or more excipients to provide an appropriate medium for one or more therapeutic agents included in an embodiment of the shaped composition 160 (e.g., for assisting in manufacture), or to preserve integrity of one or more other therapeutic agents (e.g., during manufacture, during storage, or after ingestion prior to dispersion within the body).

Examples of excipients include without limitation binders, disintegrants and superdisintegrants, buffering agents, anti-oxidants, and preservatives.

As noted above, each therapeutic formulation can include one or more therapeutic agents, and the shaped composition 160 can include one or more therapeutic formulations. Accordingly, an embodiment of the shaped composition 160 can include one therapeutic agent or multiple therapeutic agents.

A discussion will now be provided regarding enhancement formulations which may be delivered by one or more embodiments of the ingestible device 100. An enhancement formulation can include one or more delivery enhancing agents, and the shaped composition 160 can include one or more enhancement formulations. A delivery enhancing agent can, for example, serve as a delivery medium for delivery of one or more therapeutic agents or serve to improve absorption of one or more therapeutic agents into the body (e.g., a permeation enhancer, an enzyme blocker, a peptide that permeates through mucosa, an antiviral drug such as a protease inhibitor, a disintegrant or superdisintegrant, or a pH modifier.) In one or more embodiments, the delivery enhancing agent primes an epithelium of the intestine (e.g., fluidizes an outer layer of cells) to improve absorption and/or bioavailability of one or more other therapeutic agents included in the shaped composition 160 when delivered at or near the delivery location.

Examples of delivery enhancing agents include without limitation surfactants, bile salts, fatty acids, chelating agents, chitosans, and derivatives of any of the foregoing. Specific examples of delivery enhancing agents include without limitation sodium lauryl sulphate, sodium dodecylsulphate, dioctyl sodium sulfosuccinate, polysorbitate, sodium glycholate, sodium deoxycholate, sodium taurocholate, sodium dihydrofusidate, sodium glycodihdro fusidate, oleic acid, caprylic acid, lauric acid, nonylphenoxypolyoxetyylene, TWEEN® 80, medium chain fatty acid-based sodium caprate, sodium caprylate, 8-(N-2-hydroxy-5-chloro-benzoyl)-amino-caprylic acid (5-CNAC), sodium N-[8-(2-hydroxylbenzoyl)amino]caprylate (SNAC), omega 3 fatty acid acylcarnitine, acylcholine, ethylenediaminetetraacetic acid (EDTA), citric acid, salicylate, N-sulfanto-N,O-carboxymethylchitosan, N-trimethylated chloride, chitosan glutamate, alkylglycoside, lipid polymer, zonula occludens toxin, polycarbophyl-cystein conjugate, and a derivative of any of the foregoing.

An enhancement formulation can further include an excipient included to provide an appropriate medium for one or more delivery enhancing agents included in an embodiment of the enhancement formulation (e.g., for assisting in manufacture), or to preserve integrity of one or more delivery enhancing agents included in an embodiment of the enhancement formulation (e.g., during manufacture, during storage, or after ingestion prior to dispersion within the body). Excipients are described above.

In one or more embodiments, a therapeutic formulation and/or an enhancement formulation can include one or more vasodilation agents such as for example l-arginine, Sildenafil, or a nitrate (e.g., nitroglycerin).

As noted above, each enhancement formulation can include one or more delivery enhancing agents, and the shaped composition 160 can include one or more enhancement formulations. Accordingly, an embodiment of the shaped composition 160 can include one delivery enhancing agent or multiple delivery enhancing agents.

In summary, a shaped composition 160 can include: any one or more therapeutic agent(s) such as selected from the examples above in any combination; any one or more delivery enhancing agent(s) such as selected from the examples above in any combination; any one or more therapeutic formulation(s) including one or more therapeutic agents; any one or more enhancement formulation(s) including one or more delivery enhancing agents; any one or more preparation(s) combining therapeutic agents and delivery enhancing agents; one or more excipients; or any combination of any of the foregoing.

Returning to the description of FIG. 1A, the ingestible device 100 optionally includes a capability to detect when fluid breaches the outer shell 110 and reaches the delivery mechanism 102, and/or a capability to detect when the expandable enclosure 120 has expanded. For example, in one or more embodiments, electronic circuitry detects fluid, or detects expansion of the expandable enclosure 120, and wirelessly transmits a corresponding signal by way of an antenna in or on the ingestible device 100 to a device external to the ingestible device 100. Such an external device may be an electronic device implanted in the body, or may be a device external to the body. For example, the electronic circuit may transmit the signal to an implanted device, which may relay the information to a device external to the body or may store information regarding the signal (e.g., time stamp, signal identifier, strength of signal, identifier of the ingestible device 100, and other relevant information) for later download to a device external to the body. For another example, the electronic circuit may transmit the signal to a device external to the body directly. Information transmitted directly or indirectly external to the body may be received at the device external to the body and arrange for display at a graphical user interface (GUI). For example, the information may be displayed at a GUI of the external device, such as for viewing by the subject or a caregiver or physician. By detecting and signaling the ingress of fluid and/or the expansion of the expandable enclosure 120, a status of the outer shell 110 and/or the expandable enclosure 120 may be monitored as the ingestible device 100 progresses through the body.

An example of electronic circuitry to detect fluid includes two electrodes placed in close proximity to each other such that fluid present between the two electrodes causes a change (e.g., in resistance, capacitance, inductance, impedance, or reactance), which is detectable by other components in the electronic circuitry. Another example of electronic circuitry to detect fluid includes two contacts separated by a degradable material such that when the degradable material is exposed to fluid it degrades and allows the two contacts to touch and thereby complete an electrical circuit, which is detectable by other components of the electronic circuitry.

An example of electronic circuitry to detect expansion of the expandable enclosure 120 includes a thin conductor stretched along a portion of the expandable enclosure 120 such that, when the expandable enclosure 120 expands, the thin conductor breaks thus breaking a circuit, which is detectable by other components of the electronic circuitry. Another example of electronic circuitry to detect expansion of the expandable enclosure 120 includes a fluid detector positioned on the expandable enclosure 120 such that, prior to expansion, the fluid detector is covered and protected by the expandable enclosure 120 due to a folding of the expandable enclosure 120 as disposed within the outer shell 110 when manufactured; when the expandable enclosure 120 expands, the fluid detector is exposed to fluid which has breached the outer shell 110. Yet another example of electronic circuitry to detect expansion of the expandable enclosure 120 includes a fluid detector positioned between portions of the separation barrier 140 (e.g., between the first separation barrier portion 542 and the second separation barrier portion 544 in the embodiment of FIG. 5B) which fluid detector is exposed to fluid after partial or full degradation of the separation barrier 140, indicating that expansion of the expandable enclosure 120 has been initiated or will be initiated soon.

In FIG. 1A, two examples of placement of electronic circuitry are provided. As will be readily apparent, placement of electronic circuitry may be at numerous other locations within the ingestible device 100. Placement may be determined, for example, based on ease of manufacture, avoidance of interference with operation of the ingestible device 100, type of detector, and/or occurrence to be detected. In FIG. 1A, an example of an electronic circuitry 180 is shown positioned on the expandable enclosure 180 to detect fluid and/or to detect expansion of the expandable enclosure 180. An antenna 181 is electrically connected to the electronic circuitry 180. The antenna 181 is positioned on the expandable enclosure 180 such that it can stretch without breaking as the expandable enclosure 120 expands (e.g., in the arcuate sequence illustrated, which can stretch at its limits to approximately a straight line). Also in FIG. 1A, an example of an electronic circuitry 185 is shown positioned on an inner layer or inner surface of the outer shell 110 to detect fluid ingress. An antenna 186 is electrically connected to the electronic circuitry 185. The antenna 186 is, for example, a straight-line antenna, a multi-arm antenna, or a coil antenna. The antenna 186 may be disposed on the inner layer or surface of the outer shell 110, or between layers of the outer shell 110.

The discussion now continues with FIGS. 1B-1F, illustrating progression of the ingestible device 100 through various states or stages during continued traversal through the GI tract to a delivery location (e.g., to a target delivery location) within the body.

Figure 1B:
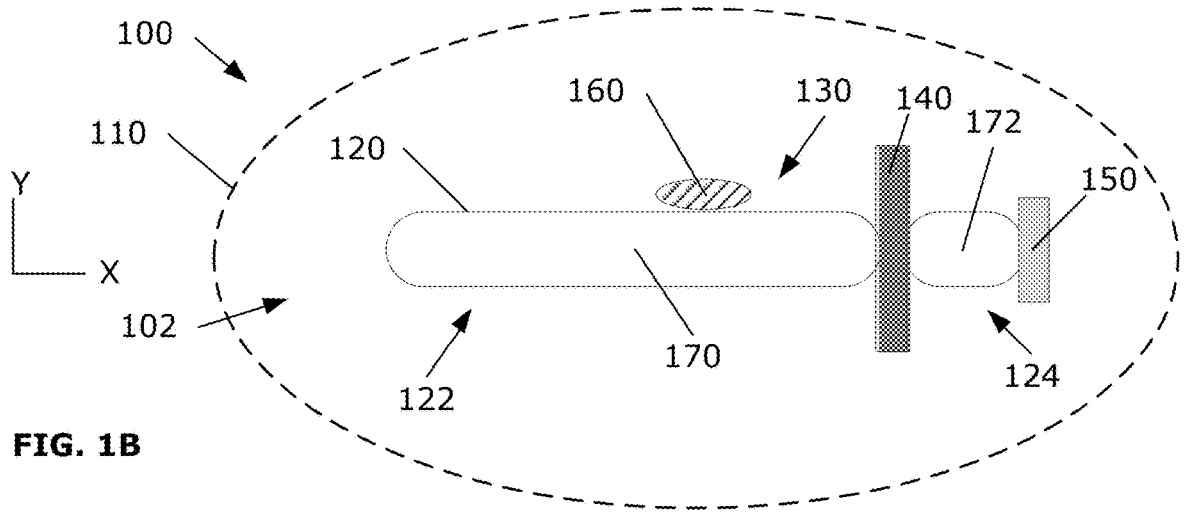

FIG. 1B illustrates the ingestible device 100 in a state in which the outer shell 110 no longer provides a barrier against digestive matter. Accordingly, in this state, the outer shell 110 exposes the remaining components of the ingestible device 100 to digestive matter. The separation barrier 140, the seal 150, and the shaped composition 160 can be structured to begin degrading upon such exposure, or to withstand degrading for respective designed amounts of time (e.g., at respective rates of degrading) after such exposure, as discussed below.

In one or more embodiments, portions of the expandable enclosure 120 as disposed within the ingestible device 100 during manufacture can be folded over or otherwise shield the shaped composition 160. For example, shielding the shaped composition 160 may prevent or slow degrading of the shaped composition 160 until the expandable enclosure 120 has expanded.

Figure 1C:
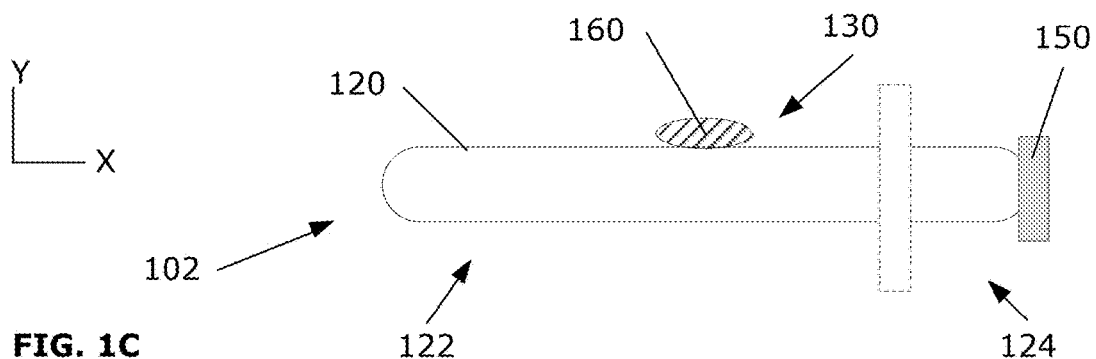

In the embodiment illustrated in FIG. 1C, the separation barrier 140 has disengaged (e.g., as a result of degrading due to exposure to digestive matter) such that the separation barrier 140 no longer acts to divide the head region 122 and the tail region 124. As such, in embodiments in which the expansion mechanism is implemented by chemical reaction, the chemical reactants contained within the head region 122 and the tail region 124 mix and chemically react to create a solution (e.g., effervescent solution) that produces a gas (e.g., including carbon dioxide).

Figure 1D:
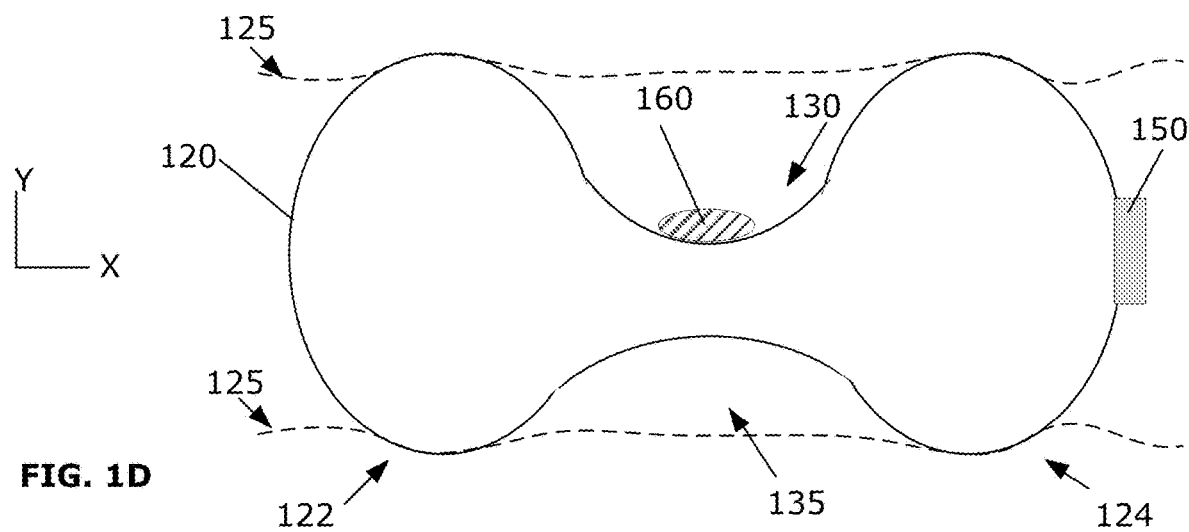

In the embodiment illustrated in FIG. 1D, the gas produced by the chemical reaction causes the expandable enclosure 120 to expand. lithe expandable enclosure 120 is considered to be aligned along the X-axis (e.g., as illustrated in FIGS. 1A-1F), expansion of the expandable enclosure 120 (e.g., FIG. 1D and FIG. 1E) can be perpendicular to the X-axis (in Y-Z directions within the X-Y-Z space) and/or along the X-axis.

As illustrated in FIG. 1D, different regions of the expandable enclosure 120 as expanded can have different dimensions, such as different cross-sectional areas, different circumferences, different diameters perpendicular to the X-axis, or different radii perpendicular to the X-axis. In one or more embodiments, the expandable enclosure 120 as expanded is reminiscent of a weightlifter's dumbbell or barbell when viewed three-dimensionally.

In one or more embodiments, a material of the expandable enclosure 120 stretches during expansion and an amount of stretch is controlled at different portions of the expandable enclosure 120 to achieve a desired resultant shape. Examples of such embodiments are illustrated and described with respect to FIGS. 4A-4C. In other embodiments, the expandable enclosure 120 is formed from a stretch-resistant material, the expandable enclosure 120 is formed in a desired shape during manufacture, and the shape is largely retained such that the shape is similar before and after expansion. In yet further embodiments, the expandable enclosure 120 is formed from stretchable material, and a shape of the expandable enclosure 120 after expansion is reminiscent of the shape of the expandable enclosure 120 before expanding, but the shape is modified by the stretching of the material.

In one or more embodiments, at least one of the head region 122 and the tail region 124 expand to contact a surface within the GI tract to temporarily anchor the expandable enclosure 120 at the delivery location (e.g., at or near the target delivery location). The head region 122 and/or the tail region 124 may press against the surface, and may extend the surface where contacted, for improved anchoring, and/or to provide a barrier to prevent or minimize a flow of digestive matter from passing and thereby shield the therapeutic composition 160.

In one or more embodiments, both the head region 122 and the tail region 124 expand to contact a surface within the GI tract, as illustrated in FIG. 1D by dotted lines 125 representing a portion of a three-dimensional surface in the GI tract. In this way, the expandable enclosure 120 forms a protective recess between the expanded head region 122 and the expanded tail region 124 when expanded, bounded in situ by the surface within the GI tract. The protective recess is a volume circumferentially around the expandable enclosure 120 between the head region 122 and the tail region 124, such as a volume circumferentially around the retention region 130. For example, when the expandable enclosure 120 is expanded in situ and aligned along the X-axis as illustrated in FIG. 1D, the volume can begin from the exterior of the expandable enclosure 120 along the retention region 130 and extend outward in Y-Z directions in the X-Y-Z space. The protective recess in situ is then bounded by the head region 122, the tail region 124, the retention region 130 of the expandable enclosure 120, and the surface of the GI tract opposite the retention region 130. For example, FIG. 1D illustrates a protective recess 135 bounded by the surface represented by dotted lines 125 defining a protective volume. A shaped composition 160 within the protective recess 135 could be shielded for a time sufficient to effectuate a transport of therapeutic agent(s) in the shaped composition 160 through the surface of the GI tract. For example, if the expandable enclosure 120 were expanded within the jejunum, therapeutic agent(s) in the shaped composition 160 may be shielded for a time sufficient to effectuate a transport of the therapeutic agent(s) through an interior wall of the jejunum to reach vascularized areas of the jejunum wall (and potentially vascularized areas in the peritoneum or areas in the peritoneum containing lymphatic vessels in the peritoneal cavity).

Figure 1E:
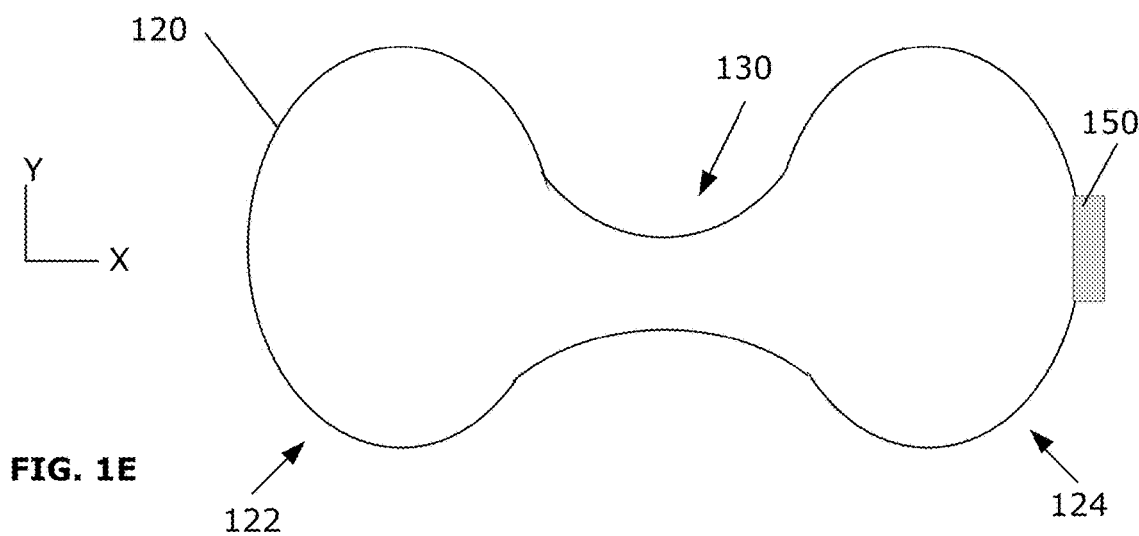

In the embodiment illustrated in FIG. 1E, the shaped composition 160 has degraded. The seal 150 continues to provide a fluid barrier between an interior of the expandable enclosure 120 and an exterior of the expandable enclosure 120 for an engagement time. Thus, in one or more embodiments, the seal 150 maintains a pressure within the expandable enclosure 120 by preventing the gas created by the chemical reaction from escaping the expandable enclosure 120. In addition, the rate of degrading of the seal 150 can be designed such that the seal 150 withstands degrading sufficiently enough to maintain its integrity and, in turn, to maintain the expandable enclosure 120 in its expanded state, for a period of time until the shaped composition 160 has degraded, and for a time thereafter to allow therapeutic agents and/or delivery enhancing agents released from the shaped composition 160 to perform their desired functions.

Figure 1F:
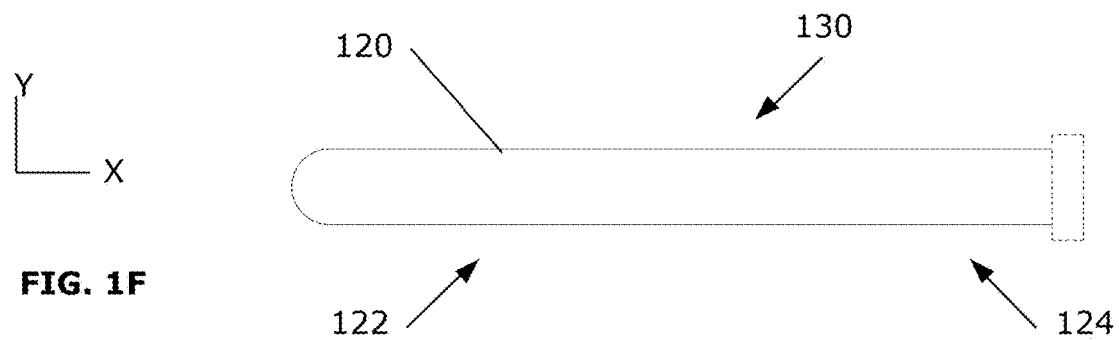

In the embodiment illustrated in FIG. 1F, the seal 150 is shown disengaged (e.g., as a result of degrading due to exposure to digestive matter) to allow the gas created from the chemical reaction to escape from an interior of the expandable enclosure 120 into the body. As such, the expandable enclosure 120 deflates and continues to pass through the body.

Figure 2:
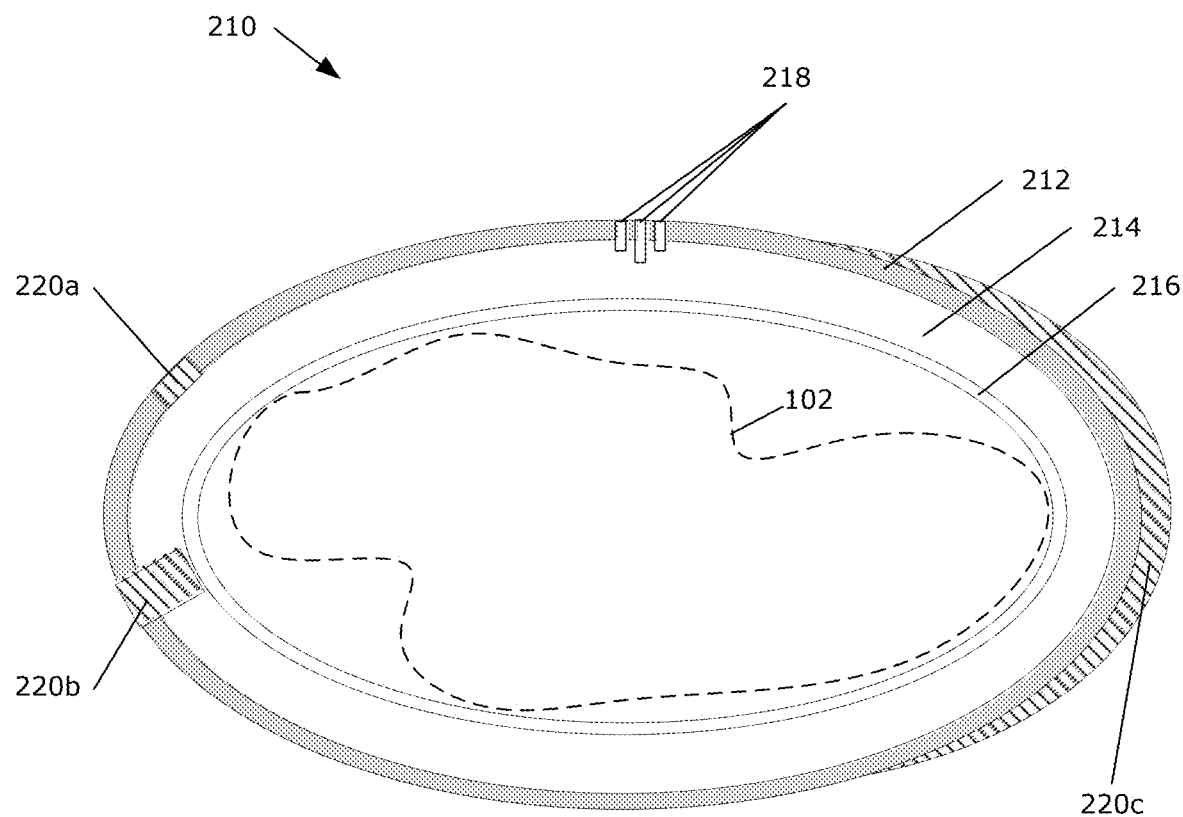
FIG. 2 illustrates an embodiment of an outer shell of an ingestible device.

FIG. 2 illustrates an example of an outer shell 210 (an embodiment of the outer shell 110 in FIG. 1A) of the ingestible device 100. The outer shell 210 is shown in cross-section along a length of the outer shell 210. Illustrated in dotted line in FIG. 2 is an outline representing an embodiment of the delivery device 102 as disposed within the outer shell 210 (e.g., after folding, rolling, twisting or the like).

In one or more embodiments, the outer shell 210 can be structured to include multiple layers, such as the multiple layers illustrated in FIG. 2. The layers of the outer shell 210 are presented by way of illustration, and more or fewer layers can be designed into other embodiments of the outer shell 110.

In one or more embodiments, the ingestible device 100 can be structured to be ingested orally. According to such embodiments, the outer shell 210 can include an outermost layer 212 to improve swallowability (e.g., a lubricious coating). In addition, the outermost layer 212 can be structured to encourage adherence to a prescribed therapeutic regimen or to discourage ingestion of the ingestible device 100 (e.g., by children), such as by incorporating a sensation in association with oral ingestion of the ingestible device 100 (e.g., taste or smell). After ingestion, the outermost layer 212 may no longer be useful or desirable, and thus may be structured to degrade rapidly after ingestion.

In one or more embodiments, the ingestible device 100 can deliver therapeutic agents to an intestine of the GI tract. As such, the outer shell 210 can be structured and sized to traverse through the GI tract to a target delivery location (e.g., to and into the jejunum).

The outer shell 210 can include a protective layer 214 providing a fluid barrier against digestive matter, and to prevent the outer shell 210 from degrading (or minimize or retard the degrading) due to exposure to digestive matter of certain areas in the body. In one or more embodiments, a target delivery location for delivery of the therapeutic agent is within the small intestine. In such embodiments, the protective layer 214 can be structured to survive traversal through the stomach (e.g., the protective layer 214 is an enteric coating). For example, the protective layer 214 can be chemically structured to be protective against a pH expected for the lower stomach (e.g., pH<7, or pH<6.5), but degrade at a pH expected for the small intestine (e.g., pH≥7, or 6.5<pH<7.5) and, after traversal of the ingestible device 100 through the stomach, the protective layer 214 begins to degrade, or degrades at an accelerated rate, in the small intestine. As an addition or alternative for such embodiments, the protective layer 214 can be structured in thickness to survive during an expected duration that the ingestible device 100 will reside in the stomach given an expected degradation rate of the protective layer 214.

The outer shell 210 can further include an innermost layer 216 which is structured to begin degrading when exposed to conditions at or near the target delivery location. For example, the fluid barrier provided by the protective layer 214 can be structured to be compromised quickly after entry of the ingestible device 100 into the duodenum of the small intestine, whereas the innermost layer 216 can be structured to degrade over a period of time after exposure to digestive matter in the small intestine such that the ingestible device 100 may reach the jejunum. In one or more embodiments, the innermost layer 216 is a capsule (e.g., size 000 or smaller capsule), or a capsule coated to delay or slow degradation of the capsule after exposure to digestive matter. In other embodiments, the innermost layer 216 is a coating applied over the delivery mechanism 102.

The layers of the outer shell 210 are selected and structured for traversal of the ingestible device 100 to a particular target delivery location (e.g., stomach, duodenum, jejunum, ilium, or colon) and delivery of the therapeutic composition(s) 160 at or near the target delivery location.

In one or more embodiments, the outer shell 210 can include one or more structural mechanisms that can cause the outer shell 210 to degrade in a controlled manner. For example, a structure of the outer shell 210 can include one or more breaks 218 (e.g., cut lines or pinholes) extending partially through the protective layer 214 to promote degradation of the outer shell 210 at particular areas of the outer shell 210, and/or one or more control segments 220 positioned to inhibit degradation of the outer shell 210 at particular areas of the outer shell 210 (embodiments illustrated as a control segment 220a covering an area of the protective layer 214, a control segment 220b covering an area of the innermost layer 216, and a control segment 220c covering an area of the outermost layer 212). An example of a material used for a control segment 220 is a wax.

For example, although a design thickness of the protective layer 214 can be uniform, an actual thickness of the protective layer 214 as manufactured may not be uniform such that the protective layer 214 tends to be thicker in certain areas of the outer shell 210 as manufactured. For such ingestible devices 100, one or more breaks 218 can be incorporated into a design of the outer shell 210 to promote degradation in thicker areas of the protective layer 214, and/or one or more control segments 220 can be incorporated into the design of the outer shell 210 to inhibit degradation in thinner areas of the protective layer 214.

For another example, it may be desired for the outer shell 210 to degrade in a particular manner such that when the delivery mechanism 102 is exposed to digestive matter due to degradation of the outer shell 210, the expansion of the expandable enclosure 120 is allowed to proceed without portions of the outer shell 210 obstructing the expansion (e.g., prior to the outer shell 210 fully degrading). In one or more embodiments of such ingestible devices 100, one or more breaks 218 and/or one or more control segments 220 can be incorporated into the outer shell 210 to define a degradation sequence for the outer shell 210. One such degradation sequence is degradation in a central portion of the outer shell 210 and delayed or inhibited degradation on ends of the outer shell 210 so that degradation of the central portion of the outer shell 210 proceeds prior to expansion of the expandable enclosure 120, and expansion of the expandable enclosure 120 pushes the intact or semi-intact portions of the outer shell 210 in a direction away from the expandable enclosure 120 (e.g., along the X-axis). It may be desirable to avoid one or more intact control segments 220 from remaining within a protective recess formed by the expandable enclosure 120 during release of the agents in the shaped composition 160; in such embodiments, the control segments 220 can be structured with materials that degrade at a slower rate than the protective layer 214 while still degrading within a design time.

In one or more embodiments, the outermost layer 212, the protective layer 214, or an additional layer (not shown) can incorporate substances to cause the outer shell 210 to become opaque (e.g., an opacifier). Additional layers (not shown) or additional substances can be incorporated into the outer shell 210 to achieve other desired design characteristics. Further, one or more layers may be omitted.

Relative dimensions of the layers 212, 214, 216 with respect to each other and with respect to other features of the ingestible device 100 can be different than illustrated in FIG. 2, and relative dimensions and positioning of the breaks 218 and/or the control segments 220 with respect to each other and with respect to other features of the ingestible device 100 can be different than illustrated in FIG. 2.

FIGS. 3A-3G illustrate embodiments of the expandable enclosure 120 in an expanded state. Various materials can be used in the expandable enclosure 120, such as a natural polymer, a synthetic polymer, an inorganic polymer, an organic polymer, a silicone, or combinations of the foregoing. Examples of natural polymers include but are not limited to starch, sodium alginate, resin, sodium hyaluronate, xanthan gum, gelatin, gellan gum, guar gum, collagen, chitosan, cellulose, rubber, and albumin. Examples of synthetic polymers include but are not limited to hydroxypropyl methyl cellulose, hydroxypropyl cellulose, polyacrylic acid, carbomers, sodium hyaluronose, chitosan, cyclodextrins, polygalacturonic acid, nylon, polyurethane, xyloglucan, xanthan gum, gellan gum, polyortho esters, hydroxyl ethyl cellulose, polyvinyl alcohol (PVA), poly(glycolic acid) (PGA), polylactic acid (PLA), polycaprolactone (PCL), and polytetrafluoroethylene (PTFE).

In one or more embodiments, the expandable enclosure 120 can be constructed in multiple layers to impart desired characteristics to the expandable enclosure 120. For example, a mesh (e.g., a metal or polymer mesh) can be incorporated as a layer in a portion of the expandable enclosure 120 for strength and resistance to stretch, whereas other layers can be incorporated with or around the mesh such as to provide a fluid barrier and/or to allow for sealing edges of the expandable enclosure 120 together.

A shape of the expandable enclosure 120 as expanded can be designed, such as: by designing a shape of a template for material(s) used to create the expandable enclosure 120; by selecting material(s) for different portions of the expandable enclosure 120 based on an amount the selected material(s) are expected to stretch when expanding; by varying a thickness of material(s) in different portions of the expandable enclosure 120 to control stretching of the material(s) in the different portions relative to each other; by incorporating a constricting mechanism in or circumferentially around areas of the expandable enclosure 120 to inhibit expansion in such areas; or by other techniques; or by any combination of the foregoing. Accordingly, material(s) used in the expandable enclosure 120 can be selected based on a stretch metric among other characteristics. In one or more embodiments, other characteristics contemplated in a selection of a material can include a compliance metric, a metric describing an amount of pressure the material can withstand (e.g., due to pressure during expansion of the expandable enclosure 120 or after the expandable enclosure 120 is expanded), a metric describing how the material can be sealed to form the expandable enclosure 120, or other characteristics desirable for the material.

In one or more embodiments, a circumference of a portion of the expandable enclosure 120 before expansion is approximately the same as the circumference of that portion of the expandable enclosure 120 after expansion; in other embodiments, a circumference before expansion can increase by the expansion. In one or more embodiments, a length of a region of the expandable enclosure 120 before expansion is approximately the same as the length of that portion of the expandable enclosure 120 after expansion; in other embodiments, a length before expansion can increase by the expansion.

Figure 3A:
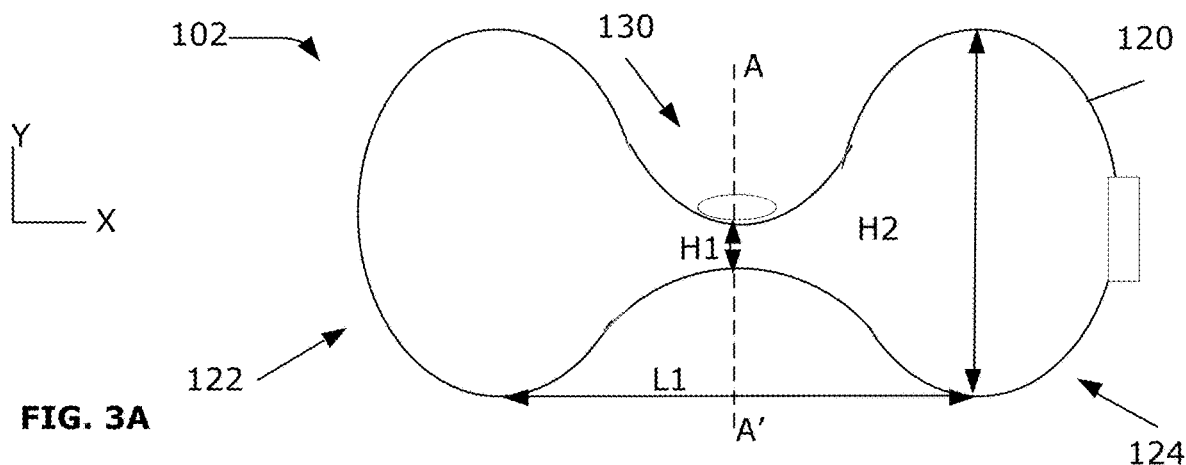
FIG. 3A, FIG. 3B, FIG. 3C, FIG. 3D, FIG. 3E, FIG. 3F, and FIG. 3G illustrate embodiments of an expandable enclosure of an ingestible device.

In the embodiment of FIG. 3A, the expandable enclosure 120 is structured by design such that, when expanded, the retention region 130 has an approximate length L1 and non-uniform height (e.g., heights in a range between a height H1 and a height H2).

As illustrated by the embodiment in FIG. 3A, the expandable enclosure 120 can be symmetric so that a shape of the head region 122 can mirror a shape of the tail region 124 in relation to a central axis A-A' when the expandable enclosure 120 is expanded; in other embodiments, the expandable enclosure 120 can be asymmetric before and/or after expansion. Further, in one or more embodiments, the expandable enclosure 120 can be symmetric or asymmetric around the X-axis.

Figure 3B:
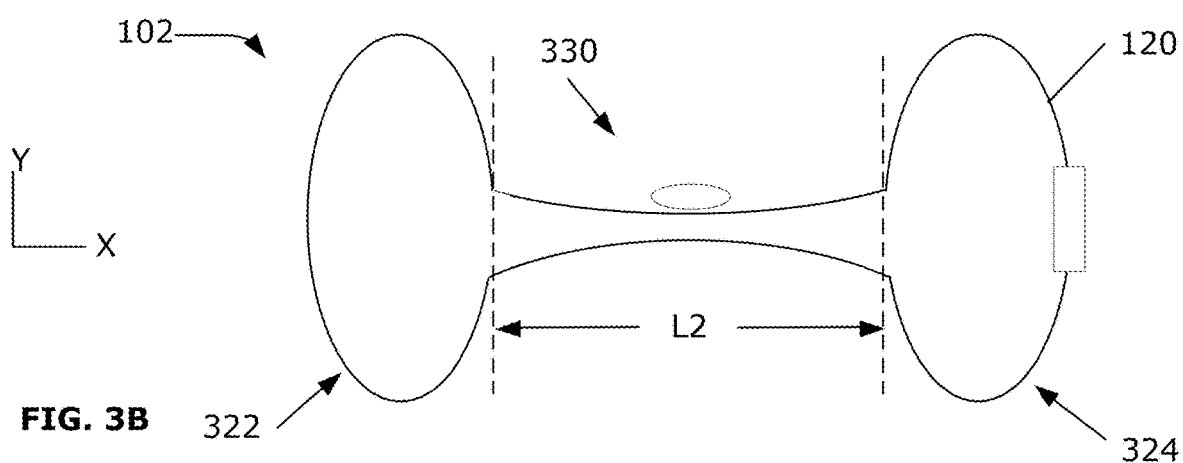

In the embodiment of FIG. 3B, the expandable enclosure 120 includes a retention region 330 with an approximate length L2 between a head region 322 and a tail region 324. The length L2 of the retention region 330 in FIG. 3B is longer than the length L1 of the retention region 130 in FIG. 3A. The longer length of the retention region 330 can provide for a greater area in which a greater number of shaped compositions can be disposed (e.g., for a higher delivery dosage per ingestible device 100), or a greater size of shaped composition(s), or a larger surface area of the delivery location exposed to the shaped composition(s) (e.g., for improved rate or efficacy of therapeutic agent transport).

In one or more other embodiments, a design length of the retention region 330 can be shortened so that more material of the expandable enclosure 120 can be devoted to expansion along the X-axis and/or expansion in Y-Z directions at the head region 322 and/or the tail region 324 (e.g., to accommodate a range of diameters of the GI tract at the target delivery location, or to improve a fit of the expandable enclosure 120 against an interior wall of the GI tract at the target delivery location for an improved barrier against digestive matter).

Figure 3C:
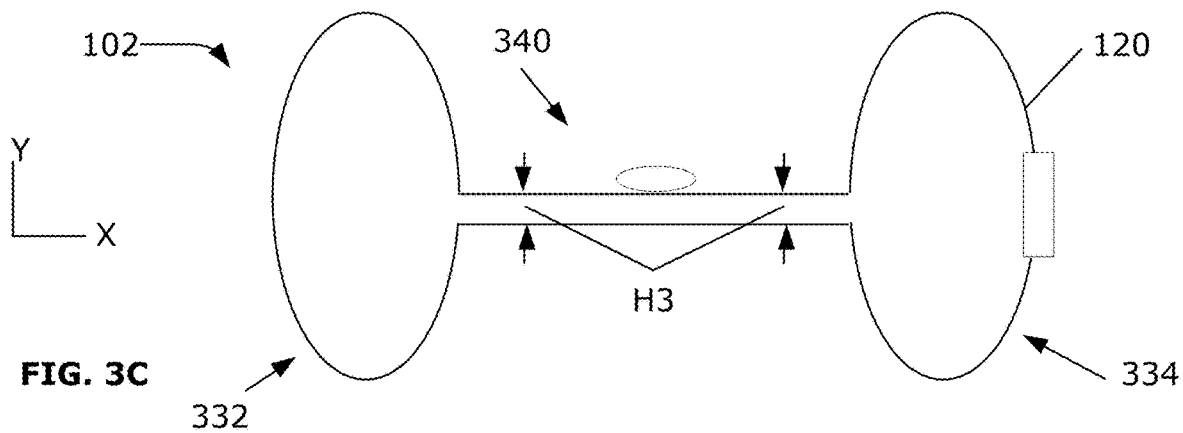

In the embodiment of FIG. 3C, the expandable enclosure 120 is structured such that a retention region 340 between a head region 332 and a tail region 334 has a uniform design height H3 when expanded. The uniform height of the retention region 340 can provide a more stable surface on which to attach or otherwise affix the shaped composition during the assembly process, if applicable, among other benefits.

Figure 3D:
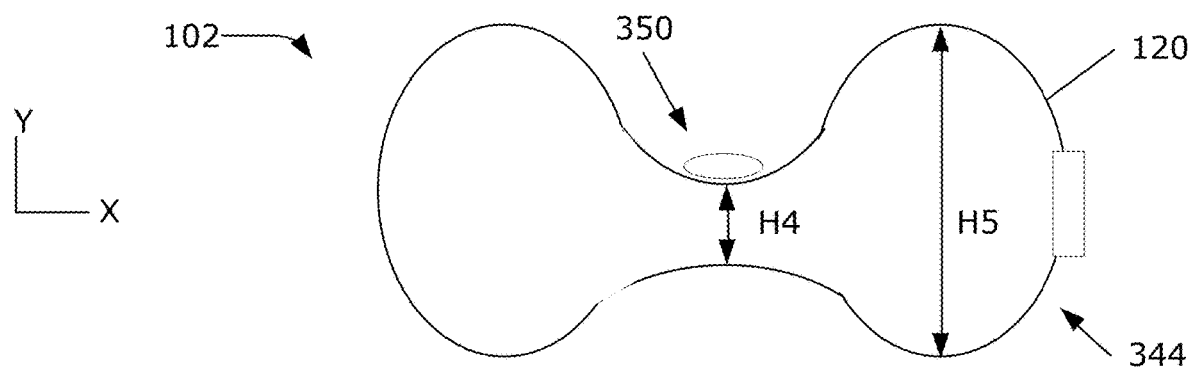

In the embodiment of FIG. 3D, the expandable enclosure 120 is structured so that a portion of a retention region 350 expands to a height H4, which is less than a height H5 of a tail region 344 but greater than the height H1 of the embodiment illustrated in FIG. 3A. In this way, the retention region 350 can be in closer proximity to the delivery location (e.g., a wall of the small intestine) when the expandable enclosure 120 is expanded relative to the embodiment in FIG. 1A, bringing the shaped composition 160 in closer proximity to the delivery location, which can aid in the delivery of the shaped composition 160 in one or more embodiments.

Figure 3E:
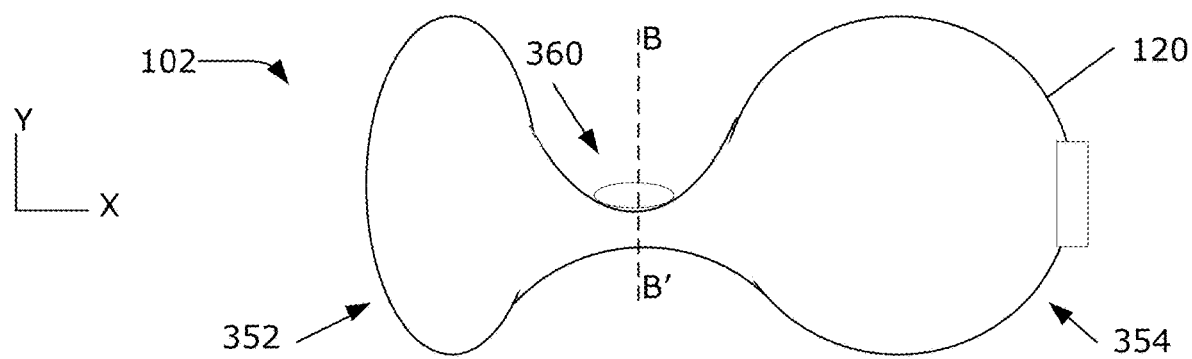

In the embodiment of FIG. 3E, the expandable enclosure 120 is structured such that a head region 352 and a tail region 354 are asymmetric in relation to an axis B-B' in a retention region 360 when the expandable enclosure 120 is expanded. In one or more embodiments, in addition or alternative, the head region 352 and/or the tail region 354 may be asymmetric with respect to the X-axis.

Figure 3F:
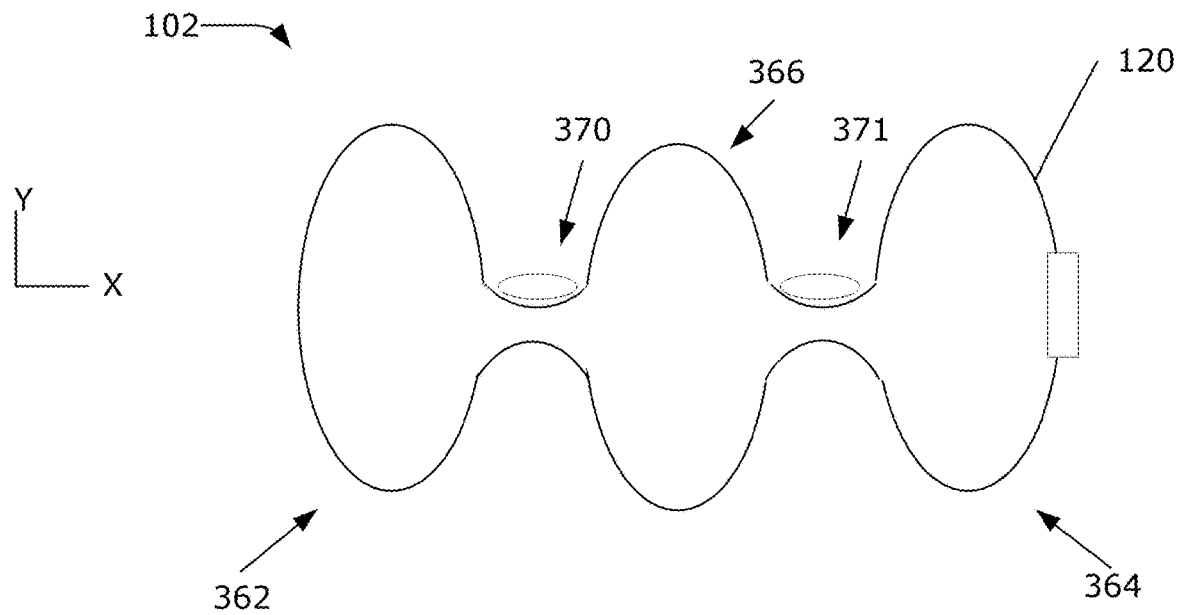

In the embodiment of FIG. 3F, the expandable enclosure 120 is structured to include a mid-region 366 between a head region 362 and a tail region 364. A retention region 370 is in a protective recess defined between the head region 362 and the mid-region 366, and a retention region 371 is in a protective recess defined between the mid-region 366 and the tail region 364.

Figure 3G:
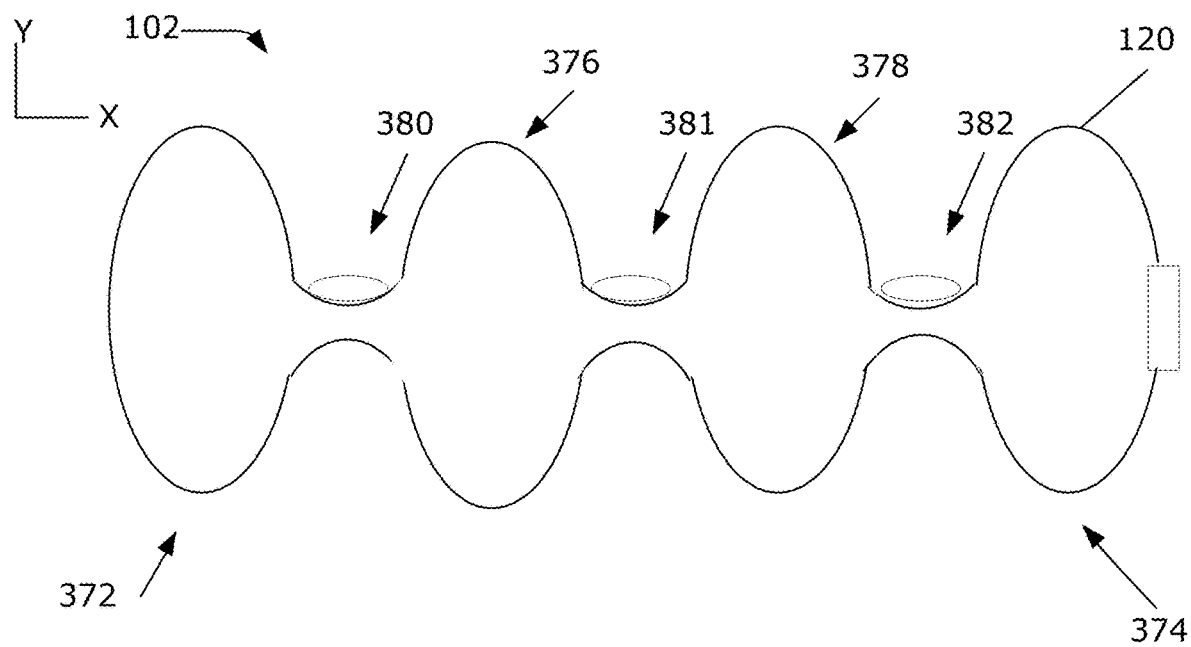

In the embodiment of FIG. 3G, the expandable enclosure 120 is structured to include a head region 372, a tail region 374, and two mid-regions 376, 378 between the head region 372 and the tail region 374. The head region 372, the two mid-regions 376, 378, and the tail region 374 together define three protective recesses in which three retention regions 380, 381, 382 are located.

Multiple retention regions (e.g., multiple retention regions 370, 371 or multiple retention regions 380, 381, 382) can provide for simultaneous delivery of multiple therapeutic agents. For example, a first retention region can include a shaped composition with a first therapeutic agent, a second retention region can include a shaped composition with a second therapeutic agent, and so forth. For another example, different retention regions can include the same therapeutic agent in similar or different forms. The multiple retention regions can provide for staged dosing, such as by providing shaped compositions with different rates of degradation in different retention regions. The multiple retention regions can provide for the delivery of higher dosages of the shaped compositions by virtue of an increased number of shaped compositions that can be contained within the ingestible device 100. The multiple retention regions can provide for delivery of different types of shaped compositions within different retention regions or different combinations of shaped compositions within different regions.

Multiple (e.g., multiple retention regions 370, 371 or multiple retention regions 380, 381, 382) can provide for adaptation to movement of a delivery device through the GI tract in response to peristaltic action within the GI tract. For example, a first formulation may be disposed in a first retention region to prepare the GI tract at a delivery location (which may be a stretch of the GI tract as the ingestible device 100 is moved by peristaltic action), and a second formulation may be disposed in a second retention region which, by peristalsis, subsequently reaches the delivery location, such that the GI tract may be prepared by the first formulation and a therapeutic agent is delivered in the second formulation. Alternatively or additionally, multiple ingestible devices (e.g., two ingestible devices 100) may be ingested in succession. For example, a first ingestible device delivers a first formulation along a first stretch of the GI tract as the first ingestible device is moved by peristalsis; and a second ingestible device delivers a second formulation along a second stretch of the GI tract as the second ingestible device is moved by peristalsis; where the second stretch overlaps the first stretch. In such therapeutic regimens using multiple ingestible devices, formulations of any of the ingestible devices may be therapeutic formulations, enhancement formulations, or a combination of therapeutic formulations and enhancement formulations.

Figure 4A:
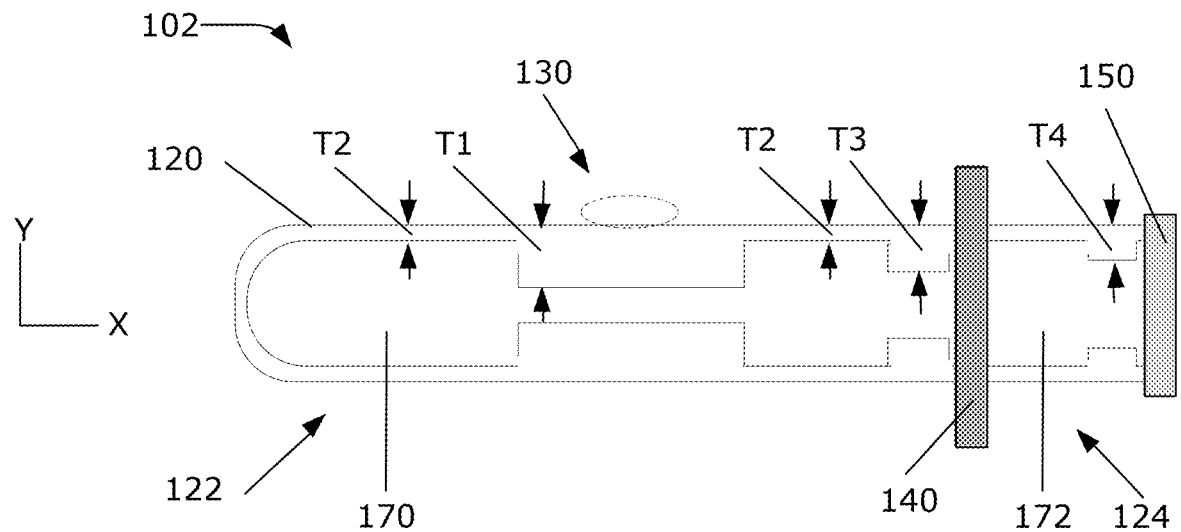
FIG. 4A illustrates an embodiment of an expandable enclosure constructed with varying thicknesses of material.
Figure 4B:
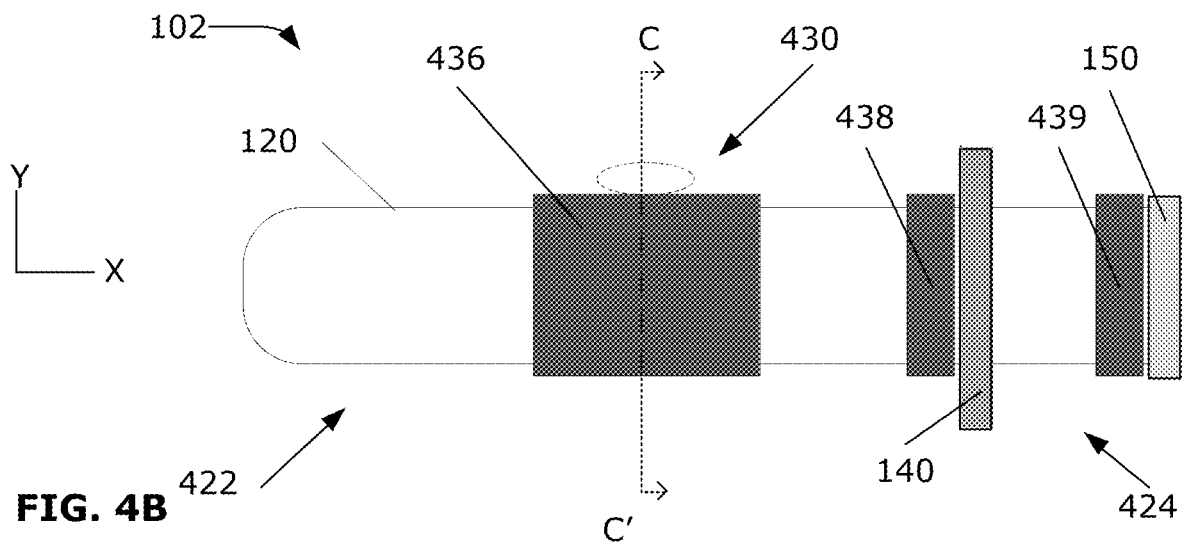
FIG. 4B illustrates an embodiment of an expandable enclosure and multiple constricting structures positioned to limit expansion of the expandable enclosure.

FIG. 4A and FIG. 4B illustrate embodiments of techniques that can be used to control an expanded shape of the expandable enclosure 120 when a material used in the expandable enclosure 120 is stretchable.

In the embodiment of FIG. 4A, the expandable enclosure 120 is structured with different thicknesses in different regions. The expandable enclosure 120 is shown in cross-section along a length of the expandable enclosure 120 to expose the different thicknesses. Greater thickness in a section can cause greater rigidity in that section and therefore more resistance to stretch.

In FIG. 4A, the retention region 130 includes a thickness T1. The thickness T1 of the retention region 130 is greater than a thickness T2 of the head region 122 and the tail region 124. As such, the greater thickness of the retention region 130 in this embodiment causes the retention region 130 to be more rigid than the head region 122 and the tail region 124, so that the head region 122 and the tail region 124 stretch more during expansion of the expandable enclosure 120. Further, the expandable enclosure 120 can include a thickness T3 at or near the separation barrier 140, and a thickness T4 at or near the seal 150. Structuring the expandable enclosure 120 to include greater thicknesses at or near the separation barrier 140 and/or the seal 150 can act to limit strain experienced at the respective separation barrier 140 and/or the seal 150 during expansion or in an expanded state.

In one or more embodiments, materials can be added circumferentially to a base material at different lateral (along the X-axis) portions of the expandable enclosure 120, where the added materials add rigidity by way of thickness or by way of the respective stretch properties of the materials. In one or more embodiments, different materials can form the expandable enclosure 120 along different lateral portions of the expandable enclosure 120 and are joined together (e.g., by adhesive, by heat joining, or by vibration joining), where one or more of the materials have different thicknesses or different stretch properties from others of the materials. In one or more embodiments, expansion is controlled by varying thickness of a single material along the expandable enclosure 120. Other embodiments are also contemplated, such as a combination of two or more of the foregoing.

In one or more embodiments, a thickness of the expandable enclosure 120 can be varied by, for example, a design of an injection mold, or by adding thickness in a controlled manner such as by dipping, dripping, or spraying material at desired locations along the expandable enclosure 120 to the desired thickness, or combinations of the foregoing.

As discussed above, in addition or alternative to controlling expansion by material thickness, a constricting structure can be used to limit expansion of the expandable enclosure 120 where desired.

In the embodiment of FIG. 4B, the delivery mechanism 102 includes a constricting structure 436 to prevent or limit expansion of a retention region 430 in relation to a head region 422 and a tail region 424 during expansion of the expandable enclosure 120, and further includes a constricting structure 438 neighboring the separation barrier 140 (on one or both sides) and/or under the separation barrier 140 and a constricting structure 439 neighboring the seal 150 (on one or both sides) and/or under the seal 150. The constricting structures 436, 438 or 439 can be formed from any type of synthetic or natural material that can pass through the human body and provide resistance to the expansion of the expandable enclosure 120 (e.g., a polymer). An amount of expansion of the expandable enclosure 120 can be regulated by several factors. For example, the amount of expansion of the expandable enclosure 120 can be regulated by a size of the constricting structure 436, 438, or 439 relative to the expandable enclosure 120 (e.g., an inner circumference of the respective constricting structure 436, 438, or 439 relative to an outer circumference of the expandable enclosure 120) and mechanical properties of the respective constricting structure 436, 438, 439 (e.g., rigidity). The constricting structure 436, the constricting structure 438, and the constricting structure 439 of FIG. 4B can perform the same or similar functions as the thickness T1, thickness T3, and thickness T4, respectively, of FIG. 4A.

In one or more embodiments, the constricting structure 436, 438, or 439 can be attached or otherwise affixed to the expandable enclosure 120 (e.g., by adhesive).

In one or more other embodiments, a constricting structure (e.g., the constricting structure 436, 438, or 439) is embedded within a material (or between material layers) forming the expandable enclosure 120.

Figure 4C:
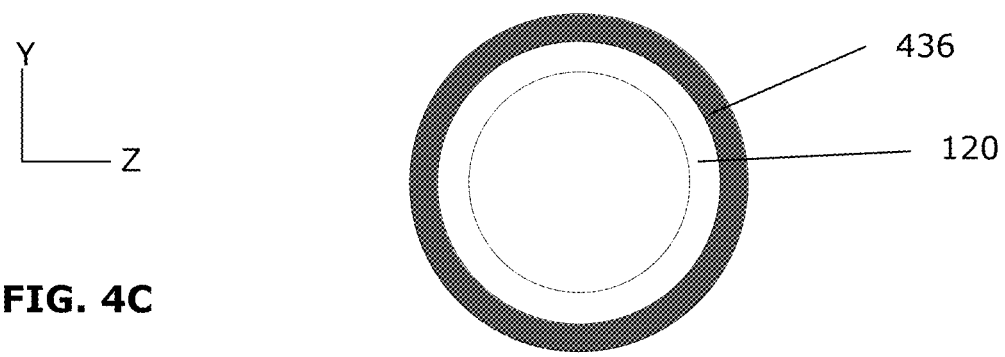
FIG. 4C illustrates an enlarged cross-sectional view of an embodiment of a portion of FIG. 4B including one of the constricting structures.

In one or more embodiments, a constricting structure may be a shaped composition structured in a shape to surround the expandable enclosure 120 (see, for example, the illustration in FIG. 4C and related discussion). Such shaped composition constricting structure can be used additionally or alternatively to other forms of shaped compositions.

Multiple retention regions (e.g., multiple retention regions 370, 371 in FIG. 3F or multiple retention regions 380, 381, 382 in FIG. 3G) may be formed using multiple shaped composition constricting structures, or one or more shaped composition constricting structure(s) in combination with one or more other type of constricting structure(s), where the shaped composition constricting structure(s) may be used additionally or alternatively to other forms of shaped compositions (e.g., shaped composition 160, 860, 870, 880, 890, 895 or other shaped composition).

FIG. 4C is an enlarged cross-sectional view of the expandable enclosure 120 along a plane indicated by a line C-C' in FIG. 4B, according to an embodiment. In the embodiment illustrated in FIG. 4C, the constricting structure 436 has an annular shape in cross-section that surrounds the expandable enclosure 120. Other cross-sectional shapes for the constricting structures 436, 438, or 439 are contemplated (e.g., a rectangular cross-section, or other shape with multiple symmetric or asymmetric sides in cross-section). A constricting structure may have a substantially uniform cross-sectional shape and dimensions along its length, or may have a cross-sectional shape and/or dimensions that vary along its length.

In one or more embodiments, portions of, or all of, the expandable enclosure 120 are fabricated as a sheet with different materials and/or different thicknesses along the sheet; the sheet is then joined on opposing sides and optionally joined to additional components to form the expandable enclosure 120. In other embodiments, a material is disposed around a forming structure such that there is a hollow area inside the material, and the material can be the expandable enclosure 120, or the material can be joined to additional components, or can be coated, to form the expandable enclosure 120. In yet further embodiments, the expandable enclosure 120 is a tube, which can be closed at one end as manufactured, or sealed during manufacture, or closed off by a mechanism such as the seal 150. In such embodiments, for example, manufacturing of the delivery device 102 can begin by cutting a length of tubing to a desired size, optionally sealing the cut portion of the tubing at one end, and optionally adding material thickness or constricting structures to control expansion.

The discussion now returns to embodiments of other features introduced with respect to FIG. 1A.

Figure 5A:
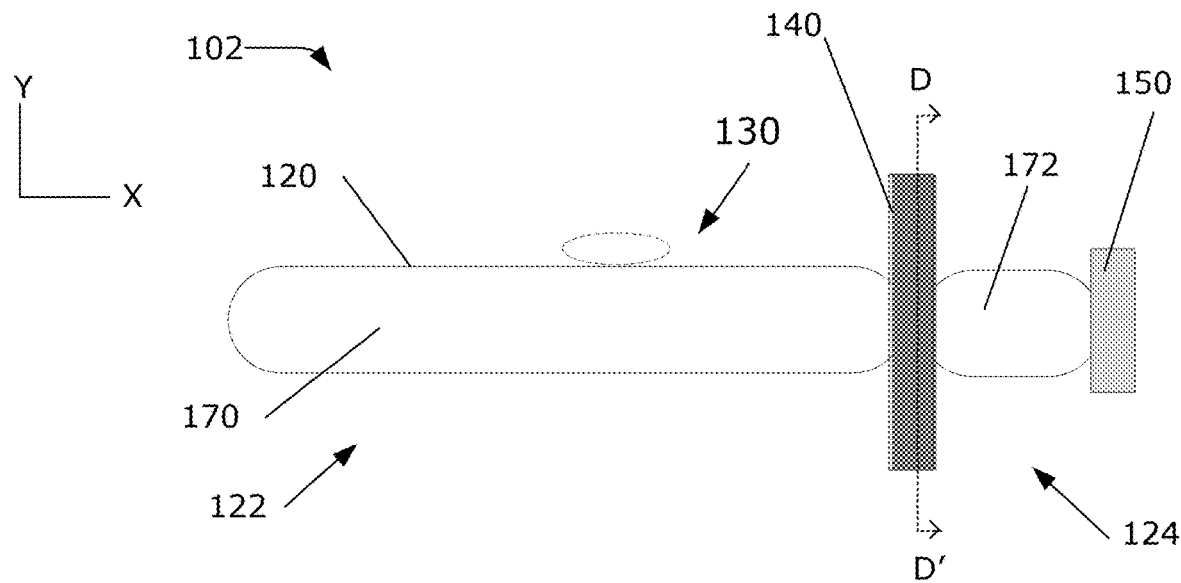
FIG. 5A illustrates an embodiment of a separation barrier of a delivery mechanism.

FIG. 5A illustrates the delivery mechanism 102 of FIG. 1A. As discussed above, the separation barrier 140 acts as a barrier between adjacent divided sections of the expandable enclosure 120. In one or more embodiments, the separation barrier 140 acts as a barrier by clamping down on or otherwise compressing together the walls of the expandable enclosure 120 to create a seal between the divided sections. Such separation barrier 140 can include a singular separation barrier body or multiple separation barrier portions.

Figure 5B:
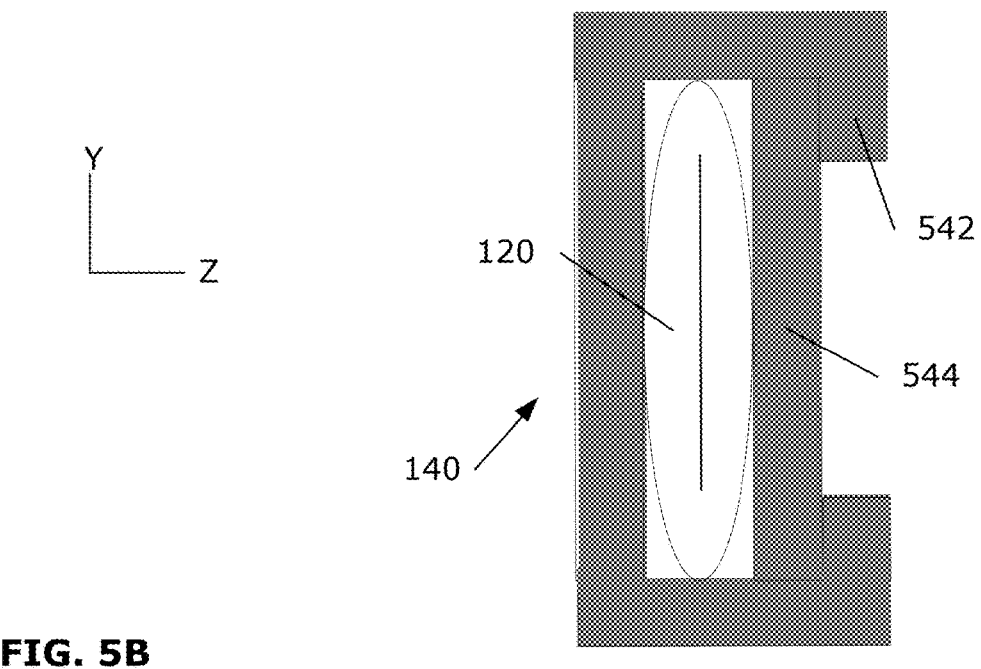
FIG. 5B is an enlarged cross-sectional view of an embodiment of a portion of FIG. 5A including the separation barrier.

FIG. 5B is an enlarged cross-sectional view of an embodiment of the separation barrier 140 along a plane indicated by a line D-D' in FIG. 5A. As illustrated in the embodiment of FIG. 5B, the separation barrier 140 includes multiple separation barrier portions, namely a first separation barrier portion 542 and a second separation barrier portion 544. The first separation barrier portion 542 and the second separation barrier portion 544 can be dimensioned and positionable relative to each other to clamp down on or otherwise compress the outer walls of the expandable enclosure 120 to cause the inner walls of the expandable enclosure to create, and form a seal between, separate regions within the expandable enclosure 120.

The separation barrier 140 can be structured to degrade upon exposure to digestive matter. After ingestion of the ingestible device 100, but before the outer shell 110 degrades sufficiently to allow digestive matter to breach an interior region of the outer shell 110, the separation barrier 140 is structured to maintain its integrity and to maintain the seal between the separate regions (e.g., containing chemical reactants, if applicable). After the outer shell 110 degrades sufficiently to allow digestive matter to breach an interior region of the outer shell 110, the components of the ingestible device 100, including the separation barrier 140, become exposed to the digestive matter. As such, the separation barrier 140 can begin to degrade upon exposure to the digestive matter.

The seal created by the separation barrier 140 can be compromised before the one or more components of the separation barrier 140 completely degrade. For example, the separation barrier 140 can weaken, and once weakened, the one or more components of the separation barrier may no longer maintain the seal, causing one or more chemical reactants (e.g., potassium bicarbonate and citric acid) within the expandable enclosure 120 to mix and chemically react to create a solution (e.g., effervescent solution) within the expandable enclosure 120.

FIG. 6A illustrates again the delivery mechanism 102 of FIG. 1A as a basis for discussing embodiments of the seal 150. As discussed above, the seal 150 provides a barrier between an interior and an exterior of the expandable enclosure 120 to prevent a gas within the expandable enclosure 120 from escaping, and/or to prevent digestive matter from entering the interior of the expandable enclosure 120. Embodiments of the seal 150 include without limitation a clamp structure (e.g., as illustrated in FIG. 6B) and a plug structure (e.g., as illustrated in FIGS. 7A-7C). Before incorporating the seal 150 with the delivery mechanism 102, an opening of the expandable enclosure 120 can provide access to the interior region of the expandable enclosure 120, such as to supply the interior region with a delivery mechanism (e.g., the chemical reactants that cause the desired expansion effect).

Figure 6A:
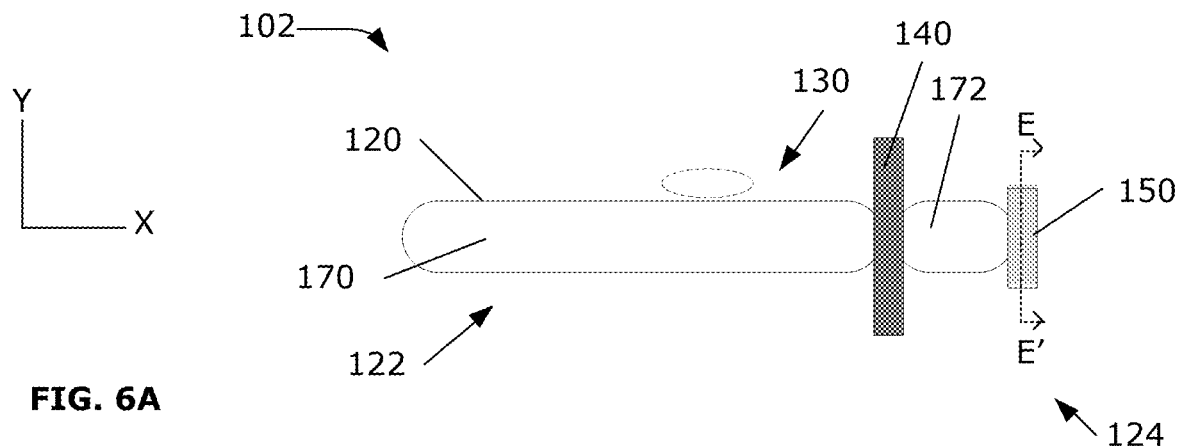
FIG. 6A illustrates an embodiment of a seal of a delivery mechanism.
Figure 6B:
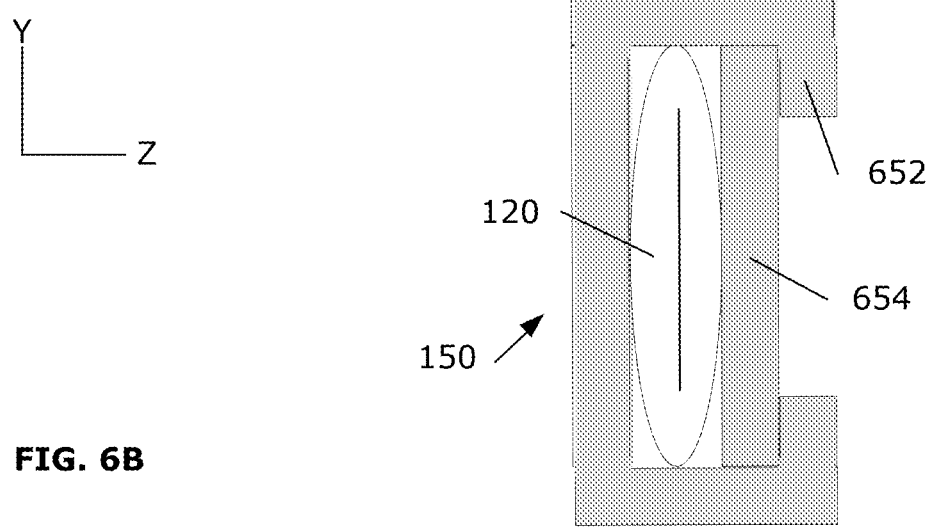
FIG. 6B is an enlarged cross-sectional view of an embodiment of a portion of FIG. 6A including the seal.
Figure 7A:
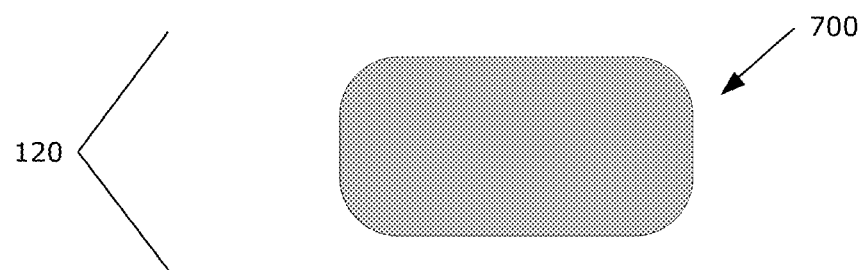
FIG. 7A, FIG. 7B, and FIG. 7C illustrate embodiments of seals, each in the form of a plug closing off respective openings of an expandable enclosure.
Figure 7B:
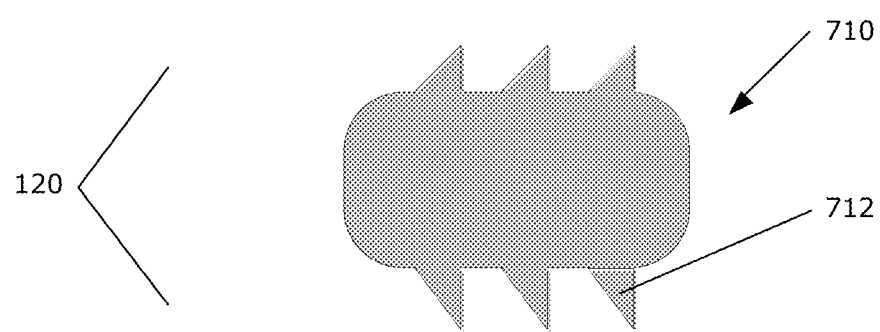
Figure 7C:
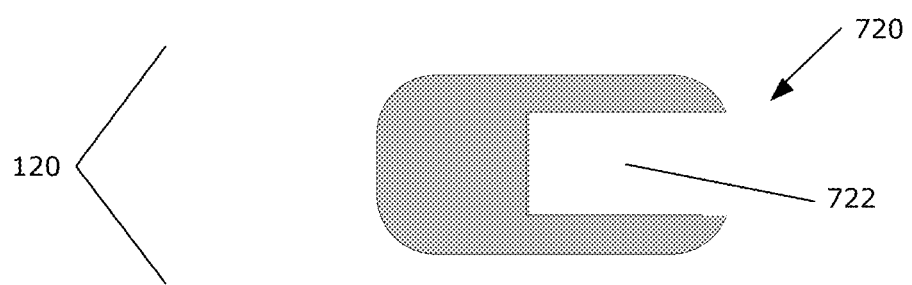

FIG. 6B is an enlarged cross-sectional view of an embodiment of the seal 150 along a plane indicated by a line E-E' in FIG. 6A. In the embodiment illustrated in FIG. 6B, the seal 150 provides the barrier by clamping down on or otherwise compressing the outer walls of the expandable enclosure 120 to cause the inner walls of the expandable enclosure 120 to form a seal at or near an opening of the expandable enclosure 120.

As illustrated in the embodiment of FIG. 6B, the seal 150 includes multiple seal portions, namely a first seal portion 652 and a second seal portion 654. The first seal portion 652 and the second seal portion 654 can be dimensioned and positionable relative to each other to clamp down on or otherwise compress the outer walls of the expandable enclosure 120 to cause the inner walls of the expandable enclosure 120 to provide a barrier between the interior and exterior of the expandable enclosure 120 at or near the opening of the expandable enclosure 120.

The seal 150 can be structured to degrade upon exposure to digestive matter. After ingestion of the ingestible device 100, but before the outer shell 110 degrades sufficiently to allow digestive matter to breach an interior region of the outer shell 110, the seal 150 is structured to maintain its integrity and to maintain the barrier between the interior and exterior of the expandable enclosure 120. After the outer shell 110 degrades sufficiently to allow digestive matter to breach an interior region of the outer shell 110, the components of the ingestible device, including the seal 150, become exposed to the digestive matter. As such, the seal 150 may begin to degrade upon exposure to the digestive matter.

A rate of degrading for the seal 150 can be slower than a rate of degrading for the separation barrier 140. In one or more embodiments, a difference between rates of degrading between the seal 150 and the separation barrier 140 can be structured selectively to achieve desired results. For example, in one or more embodiments the separation barrier 140 first disengages (e.g., as a result of degrading) so that chemical reactants separated by the separation barrier 140 can meet and chemically react, and the seal 150 can subsequently disengage (e.g., as a result of degrading) to release gas from the expandable enclosure 120. To prolong an expanded state of the expandable enclosure 120 to facilitate delivery of therapeutic agent(s) in the shaped composition 160, the seal 150 can be structured to maintain the pressure within the expandable enclosure 120 for a period of time after the integrity of the separation barrier 140 has been compromised and after the shaped composition 160 degrades.

The seal created by the seal 150 can be compromised before the one or more components of the seal 150 completely degrade. For example, the seal 150 may weaken, and once weakened, the one or more components of the seal 150 may no longer be engaged sufficiently to maintain the barrier between the interior and exterior of the expandable enclosure 120, allowing in one or more embodiments the byproduct of the chemical reaction (e.g., gas) to be released from the opening of the expandable enclosure 120, thereby deflating the expandable enclosure 120.

Figure 6C:
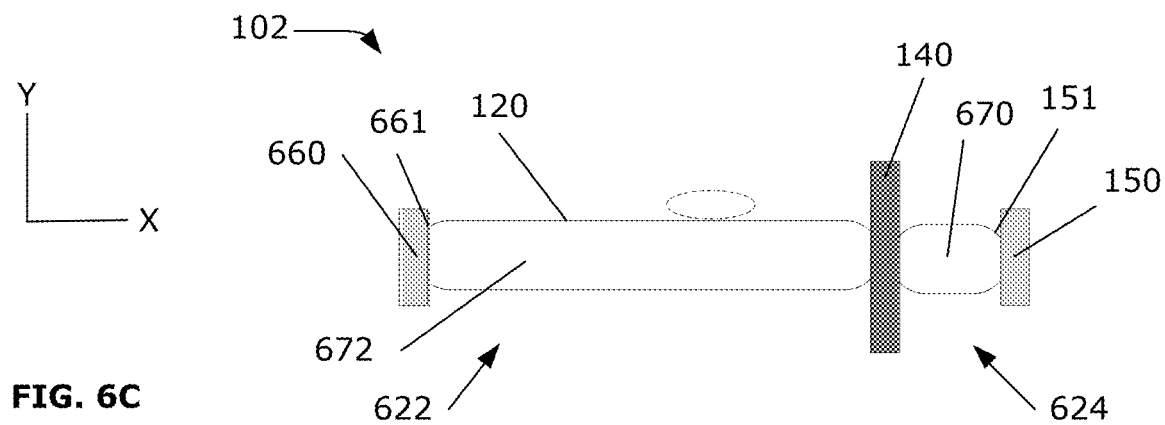
FIG. 6C illustrates an embodiment of a delivery mechanism with multiple seals.

FIG. 6C illustrates an embodiment of the delivery mechanism 102 with multiple seals closing off multiple respective openings in the expandable enclosure 120. In the embodiment illustrated in FIG. 6C, the seal 150 closes off an opening 151 at an end of the expandable enclosure 120 located in a tail region 624 to form a volume section 670, and a seal 660 closes off an opening 661 of the expandable enclosure 120 located in a head region 622 to form a volume section 672.

FIG. 7A, FIG. 7B, and FIG. 7C illustrate in cross-section various embodiments of the seal 150 in the form of a plug 700, a plug 710, and a plug 720, respectively, for use with the expandable enclosure 120.

In the embodiment of FIG. 7A, the plug 700 is inserted into an opening of an expandable enclosure 120 and retained in place by a compression fit. In the embodiment of FIG. 7B, the plug 710 includes retention features 712 extending partially around a circumference of the plug 710, or fully around the circumference of the plug 710 (e.g., flanges). The retention features 712 provide additional support to resist force exerted on the plug 710 by pressure within the expandable enclosure 120 when in an expanded state. In the illustration of FIG. 7B, the retention features 712 align with corresponding indents in the expandable enclosure 120; in implementations, the retention features 712 align with the corresponding indents within manufacturing tolerances. In one or more embodiments, the expandable enclosure 120 does not include corresponding indents, and the retention features 712 are structured for a firm fit against the expandable enclosure 120 or structured to fold over within the expandable enclosure 120 for a compression fit. In the embodiment of FIG. 7C, the plug 720 includes a cutout 722. The cutout 722 can be sized to adjust an amount of surface area of the plug 720 exposed to the digestive matter, which can decrease a design time for the plug 720 to be engaged after exposure to the digestive matter.

In each of the embodiments of FIGS. 7A-7C and other plug embodiments of the seal 150, the plug provides a fluid barrier in an opening of the expandable enclosure 120 for a designed time.

In one or more embodiments, the seal 150 can include one or more clamp valves (e.g., as illustrated in FIG. 6B) and one or more plugs (e.g., one or more of the plugs illustrated in FIG. 7A, 7B, or 7C) in combination.

As discussed above, the ingestible device 100 can include one or more shaped compositions 160 attached to the retention region 130 of the expandable enclosure 120. After the outer shell 110 of the ingestible device 100 degrades sufficiently to allow digestive matter to breach an interior of the outer shell 110, the components of the ingestible device 100, including the shaped composition 160, become exposed to the digestive matter.

FIGS. 8A-8E illustrate in cross-section some of the many embodiments of the shaped composition 160. In the illustrations of FIGS. 8A-8E, the shaped composition 160 is illustrated and discussed as including a single therapeutic agent or therapeutic formulation (for simplicity, indicated with respect to these figures as a therapeutic agent 862) and/or a single delivery enhancing agent or enhancement formulation (for simplicity, indicated with respect to these figures as a delivery enhancing agent 864) for ease of illustration and discussion. As discussed above, the shaped composition 160 can include one or more therapeutic agents and/or one or more delivery enhancing agents, each separately disposed or included in a therapeutic formulation or enhancement formulation (as applicable), or disposed in combination (e.g., in a premixed preparation, or allowed to mix after being disposed), and/or the shaped composition 160 can include one or more therapeutic formulations and/or one or more enhancement formulations. Examples of therapeutic agents and delivery enhancing agents are provided above.

Figure 8A:
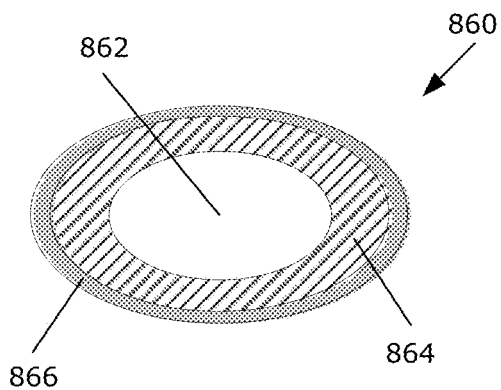
FIG. 8A, FIG. 8B, FIG. 8C, FIG. 8D, and FIG. 8E illustrate embodiments of shaped compositions.

FIG. 8A illustrates an embodiment of a shaped composition 860 including the therapeutic agent 862, the delivery enhancing agent 864, and a degradable coating 866.

In one or more embodiments, the ingestible device 100 delivers the shaped composition 860 to the intestinal tract (e.g., small intestine). In such embodiments, the delivery enhancing agent 864 can include a permeability enhancer to improve the bioavailability of the therapeutic agent 862 at a wall of the intestinal tract. For example, the permeability enhancer can improve bioavailability of the therapeutic agent 862 at the wall of the intestinal tract by fluidizing or sloughing a surface of cells (e.g., plasma membrane) of an epithelium of the intestinal tract at or near a delivery location. In one or more embodiments, the delivery enhancing agent 864 includes an enzyme blocking layer covered by a permeability enhancer layer.

The degradable coating 866 can fully or partially encase the delivery enhancing agent 864. The degradable coating 866 can include a layer to reduce or prevent degradation of the shaped composition 860 in an environment other than at the target delivery location (e.g., an enteric coating); such layer can be structured to reduce or prevent degradation by selection of a chemical composition of the layer, and/or by selection of a thickness of the layer. In addition or alternative, a rate of degradation can be designed for the degradable coating 866 for the expected environment of the target delivery location, such as by selection of chemical composition or thickness of the degradable coating 866.

In one or more embodiments, the degradable coating 866 degrades after a designed period of time or at a designed degradation rate so that the delivery enhancing agent 864 and the therapeutic agent 862 can be released when the expandable enclosure 120 is expanded and/or the expandable enclosure 120 is positioned at or near a delivery location (e.g., a target delivery location). For example, in such embodiments, the designed period of time can be greater than an expected period between a time in which the degradable coating 866 becomes initially exposed to the digestive matter and a time when the head region 122 and the tail region 124 of the expandable enclosure 120 are expanded. In one or more embodiments, the designed time can be up to one minute approximately, although shorter or longer times can be selected to accommodate characteristics of the associated ingestible device 100.

FIG. 8A illustrates a concentric structure of the therapeutic agent 862, the delivery enhancing agent 864, and the degradable coating 866 with respect to each other. Other embodiments are possible, including the embodiments illustrated in FIGS. 8B-8E.

Figure 8B:
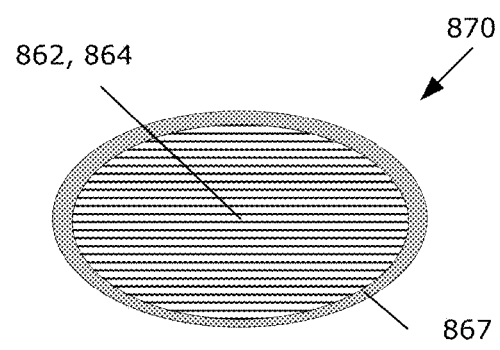

In FIG. 8B, a shaped composition 870 includes the therapeutic agent 862 and the delivery enhancing agent 864 as co-resident (e.g., combined or mixed) and encased by a degradable coating 867.

Figure 8C:
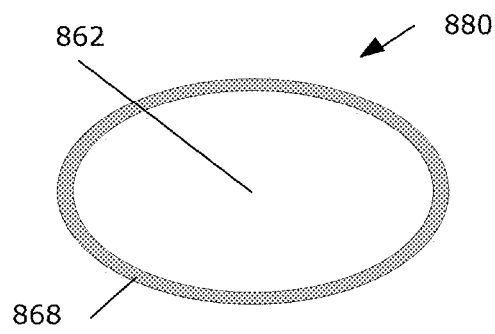
Figure 8D:
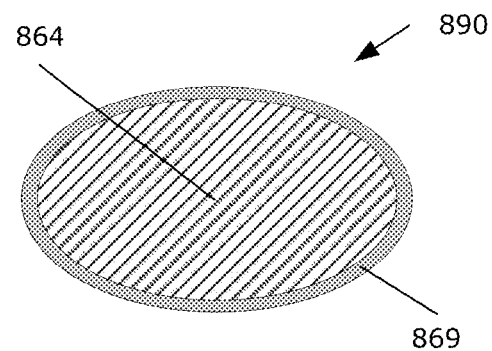

In FIG. 8C, a shaped composition 880 includes the therapeutic agent 862 encased by a degradable coating 868, without the delivery enhancing agent 864. In FIG. 8D, a shaped composition 890 includes the delivery enhancing agent 864 encased by a degradable coating 869, without the therapeutic agent 862.

In one or more embodiments, the delivery enhancing agent 864 is designed to be released before the therapeutic agent 862 in order to enhance membrane permeability of the intestinal wall and ultimately bioavailability of the therapeutic agent 862. In one or more embodiments, the ingestible device 100 includes one or more of the shaped compositions 880 (FIG. 8C) and one or more of the shaped compositions 890 (FIG. 8D), where the degradable coating 869 of the shaped composition 890 can be structured to degrade at a rate faster than the degradable coating 868 of the shaped composition 880. Further, the degradable coating 868 of the shaped composition 880 can be structured to degrade after a selected period of time from when the delivery enhancing agent 864 of the shaped composition 890 degrades. In such examples, the selected period of time can include a range of 1 to 5 minutes, approximately, although shorter or longer times are within the scope of the present disclosure.

In one or more embodiments of a shaped composition (e.g., shaped compositions 860, 870, 880, 890), the degradable coating (e.g., degradable coating 866, 867, 868, 869, respectively) can be omitted.

Figure 8E:
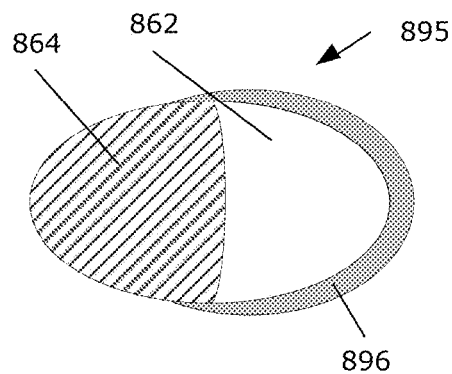

In FIG. 8E, a shaped composition 895 includes the therapeutic agent 862 disposed adjacent to the delivery enhancing agent 864, and a coating 896 over at least the therapeutic agent 862 to delay release of the therapeutic agent 862 as compared to the delivery enhancing agent 864. In one or more embodiments, the coating 896 is degradable to release the therapeutic agent 862 after a designed period of time after the shaped composition 895 is exposed to the environment at the target delivery location; in other embodiments, the coating 896 is structured to resist degradation such that the delivery enhancing agent 864 must partially or mostly release from the shaped composition 895 before the therapeutic agent 862 is exposed to the environment at the target delivery location. In one or more embodiments of a shaped composition (e.g., shaped composition 895), a degradable coating may be added.

As can be seen from the examples of FIGS. 8A-8E, there are many configurations possible for a shaped composition, and desired characteristics of the shaped composition can be incorporated by design, such as: thickness of coating(s); relative location of a therapeutic agent (or a therapeutic formulation), a delivery enhancing agent (or an enhancement formulation), and a coating with respect to each other; inclusion of more or fewer instances of therapeutic agent or therapeutic formulation, delivery enhancing agent or enhancement formulation, and coating; selection of one or more layers of a degradable coating each having selected properties; selection of a chemical composition of the degradable coating or layers thereof; selection of agents included in an enhancement formulation; selection of excipients included as part of a therapeutic formulation; and/or selection of volume or mass of the therapeutic agent(s); and many other attributes.

The ingestible device 100 can include multiple shaped compositions (e.g., one or more of the shaped compositions 860, 870, 880, 890, and/or 895). In embodiments in which multiple shaped compositions are included, the ingestible device 100 can include any number of, and any combination of, shaped compositions. For example, the ingestible device 100 can include any number of, and any combination of the shaped compositions 860, 870, 880, 890, and/or 895 or other shaped composition(s).

A shaped composition can be in the form of a pellet. For example, one or more of the shaped compositions 860, 870, 880, 890, or 895 can describe a pellet, and multiple such pellets can be separately included within the ingestible device 100, or multiple such pellets can be encased by a degradable coating to form a pellet-filled shaped composition.

Although the shaped compositions 860, 870, 880, 890, and 895 are illustrated in respective FIGS. 8A-8E with respect to each other as having similar shapes and dimensions, such illustrations are non-limiting, and different shaped compositions can have different shapes, different dimensions, and/or different constituent agents. Additionally, a volume ratio or mass ratio of therapeutic agent (or therapeutic formulation) to delivery enhancing agent (or enhancement formulation) can vary between different shaped compositions, a volume ratio or mass ratio of therapeutic agent (or therapeutic formulation) to degradable coating can vary between different shaped compositions, and a volume ratio or mass ratio of delivery enhancing agent (or enhancement formulation) to degradable coating can vary between different shaped compositions.

Figure 9A:
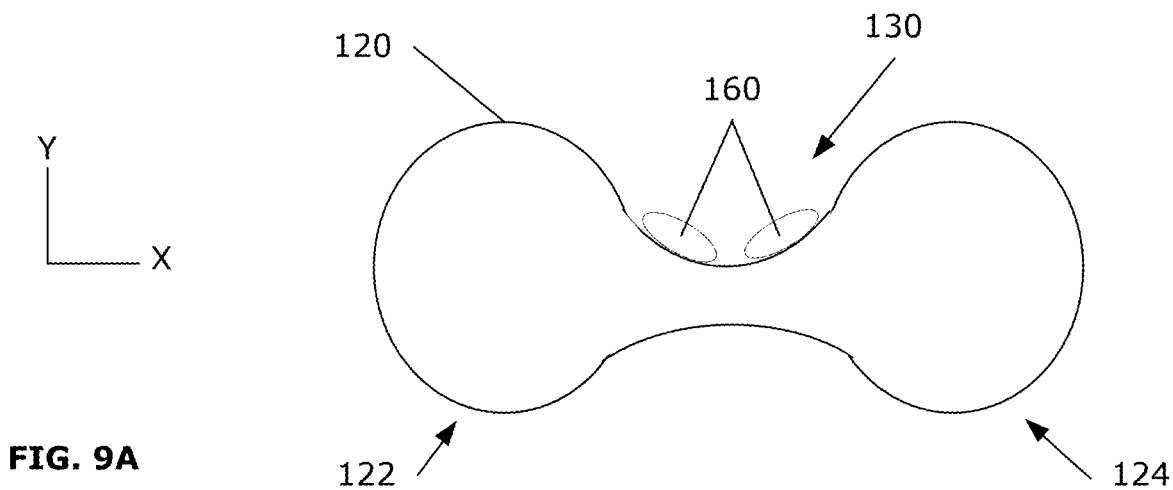
FIG. 9A and FIG. 9B illustrate embodiments of arrangements of shaped compositions at a retention region of an expandable enclosure.
Figure 9B:
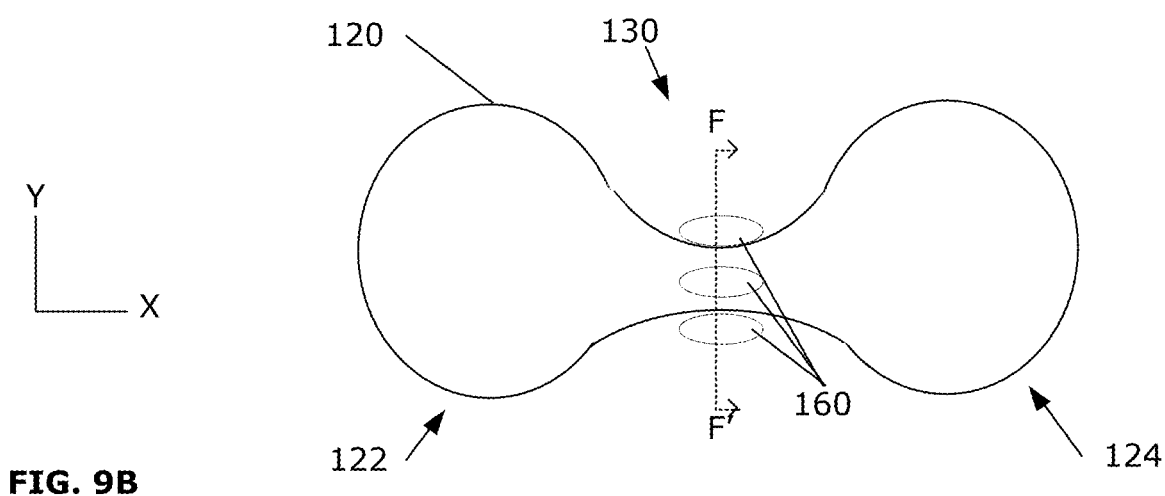
Figure 9C:
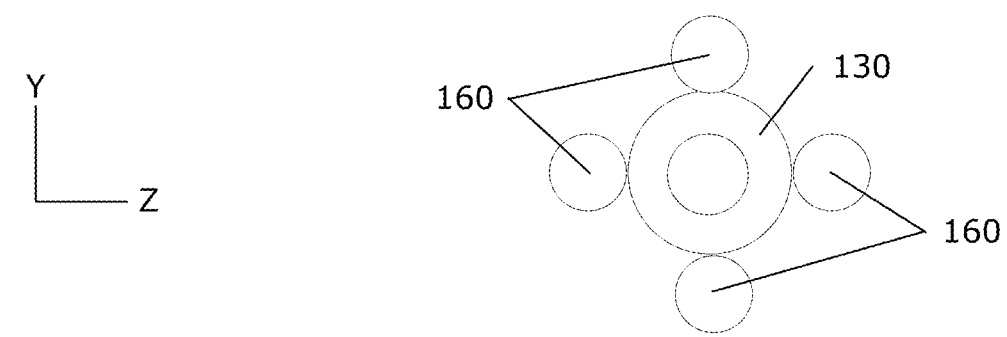
FIG. 9C illustrates an enlarged cross-sectional view of an embodiment of the arrangement in FIG. 9B.

FIG. 9A, FIG. 9B, and FIG. 9C illustrate configurations of multiple shaped compositions 160 (e.g., the shaped compositions 860, 870, 880, 890, or 895) attached or otherwise affixed to the retention region 130. For example, the shaped compositions 160 can be arranged in a side-by-side configuration on the retention region 130 (e.g., FIG. 9A), and/or the shaped compositions 160 can be attached or otherwise affixed radially around a perimeter of the retention region 130 (e.g., FIG. 9B). FIG. 9C is an enlarged cross-sectional view along a plane indicated by a line F-F' in FIG. 9B, according to an embodiment, illustrating an example of a radial arrangement of four shaped compositions 160 around the retention region 130.

Three prototype designs in accordance with the concepts described in the present disclosure are illustrated in FIGS. 10A-10E, FIGS. 11A-11D, and FIGS. 12A-12D.

In FIG. 10A, a tube 1010 (an embodiment of an expandable enclosure) is made of a flexible and stretchable material, such as silicone or a silicone-containing material. The tube 1010 includes an opening 1020.

In FIG. 10B, a first chemical reactant 1030 is disposed into the tube 1010 (through the opening 1020) and is sequestered from the remainder of the tube 1010 by a separation barrier 1040 (e.g., such as described above with respect to the separation barrier 140). In one or more embodiments, the first chemical reactant 1030 is citric acid. A shaped composition 1050 in elongated annular form is positioned around the tube 1010. The shaped composition 1050 contains a therapeutic formulation covered by one or more layers of other materials. In one or more embodiments, the shaped composition 1050 contains a therapeutic formulation covered by a permeability enhancer which in turn is covered by an enzyme blocker. The therapeutic formulation of the shaped composition 1050 may be exposed to the tube 1010 along an inner surface of the annular shaped composition 1050, if it is expected that inflation of the tube 1010 (e.g., FIG. 10D) will form a seal against fluid ingress between the inner surface of the shaped composition 1050 and the material of the tube 1010. Otherwise, the therapeutic formulation may be covered by a layer, such as one or both of the permeability enhancer layer and the enzyme blocker layer, or such as a protective layer that minimizes, reduces, or prevents degradation of the therapeutic formulation until it is exposed from the permeability enhancer layer and the enzyme blocker layer.

In FIG. 10C, a second chemical reactant 1060 is disposed into the tube 1010 (through the opening 1020), and the tube 1010 is closed and sealed by a plug 1070 (e.g., an embodiment of the seal 150, such as but not limited to plugs such as plugs 700, 710, 720 in FIGS. 7A, 7B, 7C respectively). In one or more embodiments, the second chemical reactant 1060 is potassium bicarbonate. The tube 1010 (with the plug 1070, the separation barrier 1040, the shaped composition 1050, the first chemical reactant 1030, and the second chemical reactant 1060) is folded and deposited in an outer shell (e.g., outer shell 110) (not shown) to form an ingestible device. In one or more embodiments, the outer shell includes a capsule. In one or more embodiments, the outer shell is a coating applied over the tube 1010, the plug 1070, the separation barrier 1040, and the shaped composition 1050.

In FIG. 10D, the tube 1010 is shown in a first expanded state, after the outer shell has degraded sufficiently for fluid to reach the separation barrier 1040, and after the separation barrier 1040 has degraded sufficiently for the first chemical reactant 1030 to bypass the seal previously formed by the separation barrier 1040 and combine with the second chemical reactant 1060 to form a gas (e.g., including carbon dioxide) inside the tube 1010 and thereby expand the tube 1010. When expanded, the tube 1010 defines a protective recess 1080. In situ, the protective recess 1080 is bounded by walls of the GI tract, such as shown by the dotted lines 1090 indicating an inner surface of a wall of the GI tract at a delivery location.

In FIG. 10E, the tube 1010 is shown in second expanded state, after the shaped composition 1050 has substantially degraded. The plug 1070 has not yet degraded sufficiently to allow the gas within the tube 1010 to bypass the plug 1070 into the GI tract. The plug 1070 is designed to degrade after the shaped composition 1050 has substantially degraded. For example, the shaped composition 1050 may be designed to degrade over a period of less than five minutes after initial exposure to fluid, whereas the plug 1070 may be designed to maintain integrity of the seal provided by the plug 1070 for ten to twenty minutes. After the plug 1070 degrades to the point where the seal is no longer maintained, the tube 1010 is able to deflate and pass through and out of the GI tract.

Figure 11A:
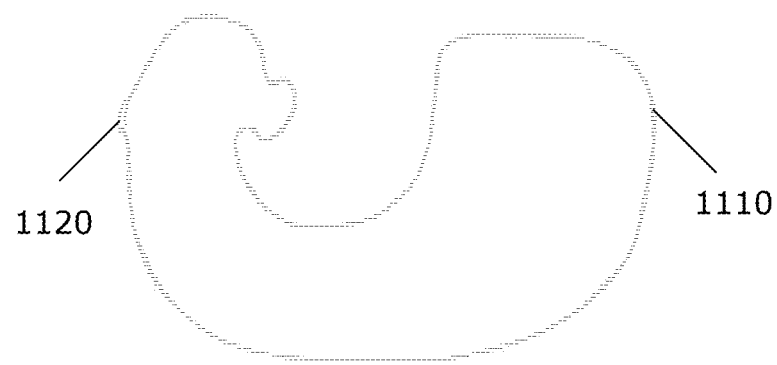
FIG. 11A, FIG. 11B, FIG. 11C, and FIG. 11D illustrate a prototype of another embodiment of an ingestible device.

In FIG. 11A, a balloon 1110 (an embodiment of an expandable enclosure) is made of a flexible and non-stretchable or fairly non-stretchable material, such as polyethylene, so that a circumference of the balloon 1110 increases little (e.g., less than fifteen percent, less than ten percent, or less than five percent) when the balloon 1110 is inflated. The balloon 1110 is formed by two similarly-shaped layers of material sealed together around a portion of the perimeter of the balloon 1110, such as two different sheets of material sealed together (and cut to shape before, during, or after sealing), or one sheet of material folded over and sealed (and cut to shape before, during, or after sealing). In one or more embodiments, sealing of the layers together is performed by using a hot knife to cut the perimeter of the shape of the balloon 1110. In one or more other embodiments, sealing of the material is performed by using heat and compression to seal the material together. In yet other embodiments, an adhesive is positioned between the layers of material to effect the seal. The balloon 1110 defines an opening 1120.

Figure 11B:
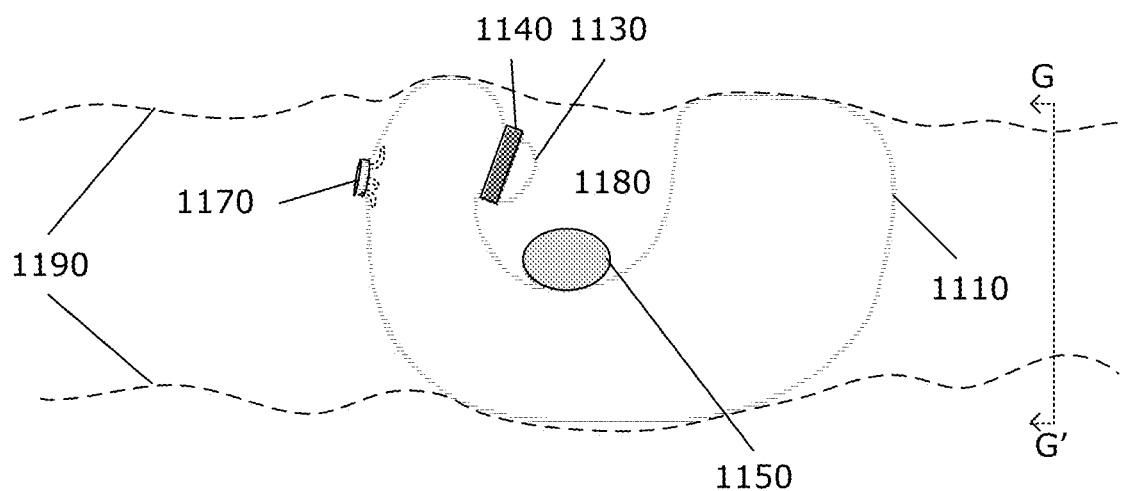

In FIG. 11B, a first chemical reactant is disposed (through the opening 1120) into a pocket 1130 defined by the balloon 1110 and is sequestered from the remainder of the balloon 1110 by a separation barrier 1140 (e.g., such as described above with respect to the separation barrier 140). In one or more embodiments, the first chemical reactant is citric acid. A shaped composition 1150 in cylindrical form is positioned on the balloon 1110 in a protective recess 1180. The shaped composition 1150 includes a therapeutic formulation covered by one or more layers of other materials. In one or more embodiments, the shaped composition 1150 contains a therapeutic formulation covered by a permeability enhancer which in turn is covered by an enzyme blocker. The enzyme blocker layer may be covered by a protective layer. A second chemical reactant is disposed (through the opening 1120) into the balloon 1110, and the balloon 1110 is closed and sealed by a plug 1170 (e.g., an embodiment of the seal 150, such as but not limited to plugs such as plugs 700, 710, 720 in FIGS. 7A, 7B, 7C respectively). In one or more embodiments, the second chemical reactant is potassium bicarbonate. The balloon 1110 (with the plug 1170, the separation barrier 1140, the shaped composition 1150, the first chemical reactant, and the second chemical reactant) is folded and deposited in an outer shell (e.g., outer shell 110) (not shown) to form an ingestible device. In one or more embodiments, the outer shell includes a capsule. In one or more embodiments, the outer shell is a coating applied over the balloon 1110, the plug 1120, the separation barrier 1140, and the shaped composition 1150. After the outer shell has degraded sufficiently for fluid to reach the separation barrier 1140, and after the separation barrier 1140 has degraded sufficiently for the first chemical reactant to bypass the seal previously formed by the separation barrier 1140 and combine with the second chemical reactant to form a gas (e.g., including carbon dioxide) inside the balloon 1110, the balloon 1110 expands. Because the material used to form the balloon 1110 is relatively non-stretchable, the circumference of the balloon 1110 expands little when the balloon 1110 is expanded. In situ, the protective recess 1180 is bounded by walls of the GI tract, such as shown by the dotted lines 1190 indicating an inner surface of a wall of the GI tract at a delivery location.

Figure 11C:
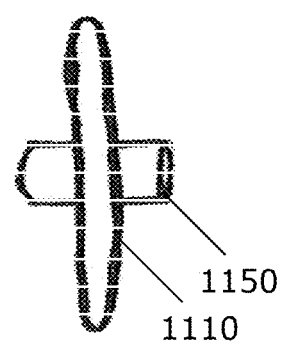

In FIG. 11C, an embodiment of the balloon 1110 and an embodiment of the shaped composition 1150 are shown from an end view (from the perspective indicated by line G-G') prior to expansion of the balloon 1100. In this embodiment, the shaped composition 1150 is cylindrically-shaped.

Figure 11D:
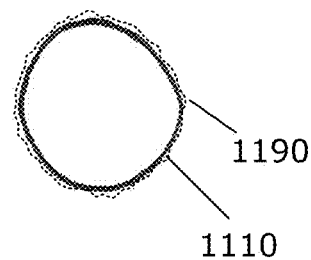

In FIG. 11D, the balloon 1110 is shown from the end view (from the perspective indicated by line G-G') subsequent to expansion of the balloon 1100. The shaped composition 1150 is no longer visible, because the balloon 1100 has expanded to contact the inner surface of the wall of the GI tract (indicated by dotted line 1190) to form the protective recess 1180.

The plug 1170 is designed to degrade after the shaped composition 1150 has substantially degraded. For example, the shaped composition 1150 may be designed to degrade over a period of ten minutes after initial exposure to fluid, whereas the plug 1170 may be designed to maintain integrity of the seal provided by the plug 1170 for fifteen to twenty minutes. After the plug 1170 degrades to the point where the seal is no longer maintained, the balloon 1110 is able to deflate and pass through and out of the GI tract.

Figure 12A:
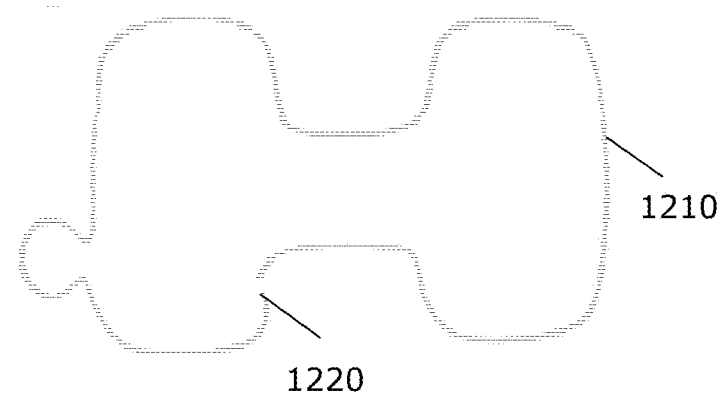
FIG. 12A, FIG. 12B, FIG. 12C, and FIG. 12D illustrate a prototype of another embodiment of an ingestible device.

In FIG. 12A, a balloon 1210 (an embodiment of an expandable enclosure) is made of a flexible and non-stretchable or fairly non-stretchable material, such as polyethylene, so that a circumference of the balloon 1210 increases little (e.g., less than fifteen percent, less than ten percent, or less than five percent) when the balloon 1210 is inflated. The balloon 1210 is formed by two similarly-shaped layers of material sealed together around a portion of the perimeter of the balloon 1210, such as two different sheets of material sealed together (and cut to shape before, during, or after sealing), or one sheet of material folded over and sealed (and cut to shape before, during, or after sealing). In one or more embodiments, sealing of the layers together is performed by using a hot knife to cut the perimeter of the shape of the balloon 1210. In one or more other embodiments, sealing of the material is performed by using heat and compression to seal the material together. In yet other embodiments, an adhesive is positioned between the layers of material to effect the seal. The balloon 1210 defines an opening 1220.

Figure 12B:
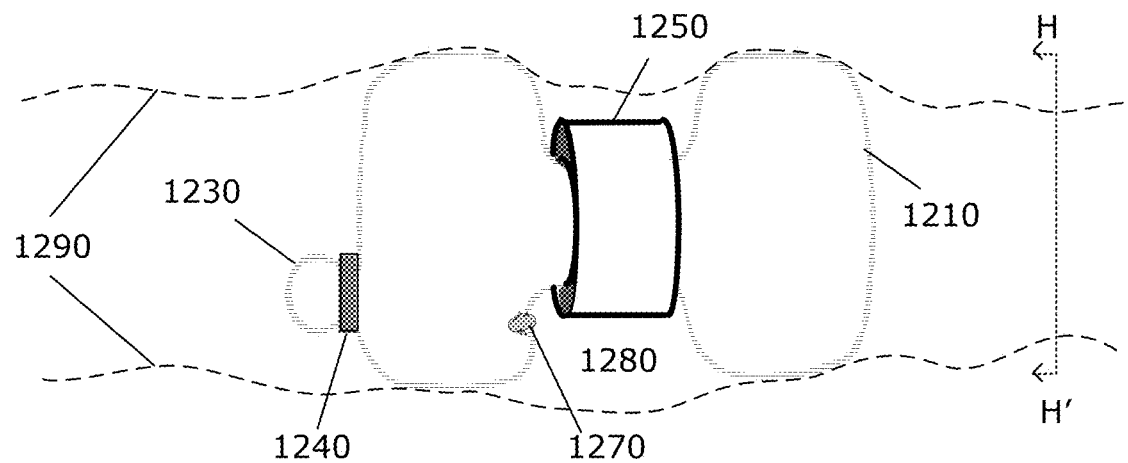

In FIG. 12B, a first chemical reactant is disposed (through the opening 1220) into a pocket 1230 defined by the balloon 1210 and is sequestered from the remainder of the balloon 1210 by a separation barrier 1240 (e.g., such as described above with respect to the separation barrier 140). In one or more embodiments, the first chemical reactant is citric acid. A shaped composition 1250 in annular form is positioned around the balloon 1210 in a protective recess 1280. The shaped composition 1250 contains a therapeutic formulation covered by one or more layers of other materials. In one or more embodiments, the shaped composition 1250 contains a therapeutic formulation covered by a permeability enhancer which in turn is covered by an enzyme blocker. The enzyme blocker layer may be covered by a protective layer. A second chemical reactant is disposed (through the opening 1220) into the balloon 1210, and the balloon 1210 is closed and sealed by a plug 1270 (e.g., an embodiment of the seal 150, such as but not limited to plugs such as plugs 700, 710, 720 in FIGS. 7A, 7B, 7C respectively). In one or more embodiments, the second chemical reactant is potassium bicarbonate. The balloon 1210 (with the plug 1270, the separation barrier 1240, the shaped composition 1250, the first chemical reactant, and the second chemical reactant) is folded and deposited in an outer shell (e.g., outer shell 110) (not shown) to form an ingestible device. In one or more embodiments, the outer shell includes a capsule. In one or more embodiments, the outer shell is a coating applied over the balloon 1210, the plug 1270, the separation barrier 1240, and the shaped composition 1250. After the outer shell has degraded sufficiently for fluid to reach the separation barrier 1240, and after the separation barrier 1240 has degraded sufficiently for the first chemical reactant to bypass the seal previously formed by the separation barrier 1240 and combine with the second chemical reactant to form a gas (e.g., including carbon dioxide) inside the balloon 1210, the balloon 1210 expands. Because the material used to form the balloon 1210 is relatively non-stretchable, the circumference of the balloon 1210 expands little when the balloon 1210 is expanded, as discussed above. In situ, the protective recess 1280 is bounded by walls of the GI tract, such as shown by the dotted lines 1290 indicating the inner surface of a wall of the GI tract at a delivery location.

Figure 12C:
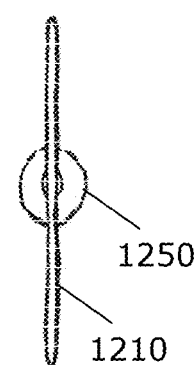

In FIG. 12C, an embodiment of the balloon 1210 and an embodiment of the shaped composition 1250 are shown from an end view (from the perspective indicated by line H-H') prior to expansion of the balloon 1200.

Figure 12D:
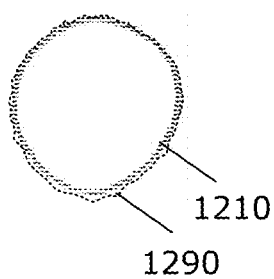

In FIG. 12D, the balloon 1210 is shown from the end view (from the perspective indicated by line H-H') subsequent to expansion of the balloon 1200. The shaped composition 1250 is no longer visible, because the balloon 1200 has expanded to contact an inner surface of a wall of the GI tract (indicated by dotted line 1290) to form the protective recess 1280.

The plug 1270 is designed to degrade after the shaped composition 1250 has substantially degraded. For example, the shaped composition 1250 may be designed to degrade over a period of ten minutes after initial exposure to fluid, whereas the plug 1270 may be designed to maintain integrity of the seal provided by the plug 1270 for fifteen to twenty minutes. After the plug 1270 degrades to the point where the seal is no longer maintained, the balloon 1210 is able to deflate and pass through and out of the GI tract.

A pressure within the tube 1010, the balloon 1110, or the balloon 1210 is sufficient to press the tube 1010, the balloon 1110, or the balloon 1210 against a wall of the GI tract.

In one or more embodiments, the pressure within an expandable enclosure is designed to be twenty pounds per square inch (PSI) or less at peak value. Testing indicates that pressure maintained at less than twenty PSI within an expandable enclosure sized with a circumference as expanded somewhat (e.g., less than fifty percent, less than twenty percent, less than fifteen percent, or less than ten percent) larger than the inner circumference of the GI tract will not be felt by a large mammal (e.g., dogs, pigs, humans). In various prototypes, pressure is maintained at approximately two PSI until the expandable enclosure deflates.

The balloon 1110 (FIGS. 11A-11D) and the balloon 1210 (FIGS. 12A-12D) may use a smaller volume or mass of the first chemical reactant and the second chemical reactant as compared to the tube 1010 (FIGS. 10A-10E), because the stretchable nature of the tube 1010 can result in a comparatively larger internal volume of the tube 1010 in relation to internal volumes of the balloon 1110 and the balloon 1210. Thus, to maintain a desired pressure, relatively more reactants may be needed in the tube 1010.

In various prototypes, a circumference of an expandable enclosure is approximately eight centimeters as expanded. In other prototypes, a circumference of an expandable enclosure is less than about ten centimeters, less than about nine centimeters, or less than about eight centimeters.

Figure 13:
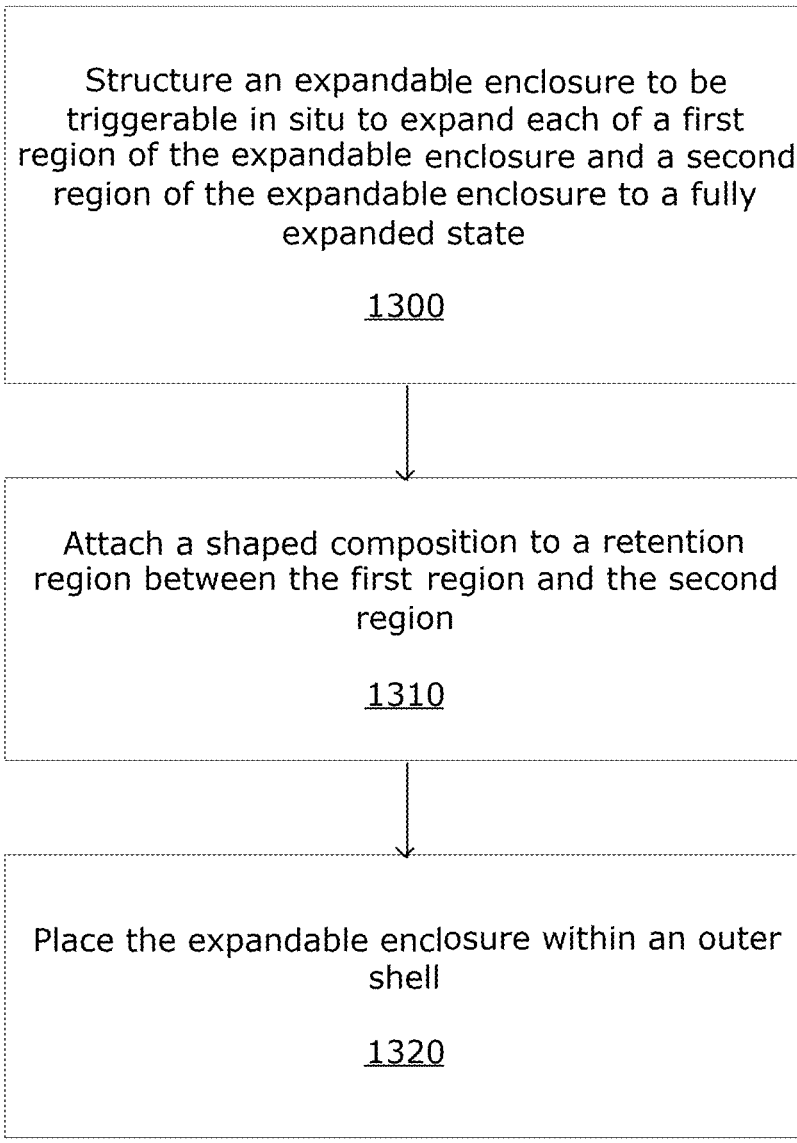
FIG. 13 illustrates an embodiment of a method for manufacturing an ingestible device.

FIG. 13 is an embodiment of a method for manufacturing an ingestible device such as examples of ingestible devices described above.

At 1300, an expandable enclosure (e.g., the expandable enclosure 120) of an ingestible device (e.g., the ingestible device 100) can be structured to be triggerable in situ to expand each of a head region (e.g., the head region 122) and a tail region (e.g., the tail region 124) of the expandable enclosure to an expanded state. The expandable enclosure can include at least one opening. The opening of the expandable enclosure can provide access to an interior of the expandable enclosure through which one or more expansion mechanisms (e.g., chemical reactants) can be supplied to the interior of the expandable enclosure. For example, a first chemical reactant (e.g., potassium bicarbonate) can be supplied to the interior of the expandable enclosure through the opening. A separation barrier (e.g., the separation barrier 140) can close off the expandable enclosure to contain the first chemical reactant. Then, a second chemical reactant (e.g., citric acid) can be supplied to the interior of the expandable enclosure through the opening. The separation barrier, in effect, divides an interior of the expandable enclosure into sections (e.g., volume sections) and acts as a barrier between the sections until the ingestible device nears a delivery location. A seal (e.g., the seal 150) can close off the expandable enclosure at or near the opening and acts as a barrier between the interior and an exterior of the expandable enclosure to prevent digestive matter from entering the interior of the expandable enclosure and to keep contents of the expandable enclosure 120 from escaping.

The separation barrier and the seal can be structured to degrade upon exposure to digestive matter at the target delivery location. In one or more embodiments, the separation barrier can be structured to degrade at a rate faster than a designed degradation rate for the seal. For example, when the separation barrier degrades from exposure to digestive matter, the separation barrier no longer acts as a barrier between adjacent sections of the expandable enclosure. As such, the chemical reactants contained in each section chemically react to create a solution (e.g., effervescent solution), the byproduct of which (e.g., gas) provides a desired expansion effect. To maintain the pressure within the expandable enclosure, the seal maintains its structural integrity so that the byproduct of the chemical reaction is not released from the expandable enclosure and the expandable enclosure remains in the expanded state for a time.

The expandable enclosure can include a retention region (e.g., the retention region 130) in a protective recess between the head region and the tail region of the expandable enclosure when expanded, which can shield the retention region from a flow of digestive matter. The retention region can be structured to have a circumference that is less than a circumference of the head region and a circumference of the tail region in the expanded state through design of the structure of the expandable enclosure or through incorporating a constricting structure within or external to the expandable enclosure.

For example, in designing the structure of the expandable enclosure, a thickness of the expandable enclosure in the retention region can be greater than a thickness of the expandable enclosure at the head region and the tail region to provide greater resistance to stretch of the expandable enclosure in the retention region. Or, in incorporating a constricting structure within or external to the expandable enclosure, the expandable enclosure can be fitted with a tube (e.g., circular, rectangular, or other cross-sectional shape, including tubes which are non-uniform in cross-section along a length of the tube) or other structure (or multiple other structures) to prevent or limit expansion in the retention region.

At 1310, one or more shaped compositions (e.g., the shaped composition 160) can be attached to the retention region. Each shaped composition can include one or more agents such as illustrated and described with respect to FIGS. 8A-8E.

The shaped composition(s) can be attached or otherwise affixed to the retention region in various arrangements. For example, shaped compositions can be arranged side-by-side (e.g., as in FIG. 9A), radially around the retention region 130 (e.g., as in FIG. 9B), stacked, or by any other arrangement or combination of arrangements.

At 1320, the expandable enclosure as part of a delivery mechanism (e.g., the delivery mechanism 102) can be placed within an outer shell (e.g., the outer shell 110). The outer shell can be structured to include a protective layer (e.g., enteric coating) designed to survive traversal through a portion of the GI tract such as the stomach. Further, the outer shell can include one or more structural mechanisms (e.g., breaks 218, control segments 220, etc.) that cause the outer shell to degrade in a particular manner or sequence.

FIG. 14 is an embodiment of a method for delivery of a therapeutic agent to a body using an ingestible device such as examples described above.

At 1400, an ingestible device (e.g., the ingestible devices 100) is provided to a subject (e.g., human or other animal). In one or more embodiments, the ingestible device is provided to the subject by a physician or the ingestible device is provided to the subject by way of a prescription that is subsequently filled; in either case, the ingestible device is provided according to a specified therapeutic regimen specified by a physician. In other embodiments, the ingestible device is provided to the subject by way of an over-the-counter purchase with a therapeutic regimen indicated on the label.

Once provided to the subject, the ingestible device may be ingested by the subject. In one or more embodiments, the ingestible device is structured to be orally ingested and traverse through the GI tract of a body. It is expected based on surveys that, because the ingestible device may be taken orally, compliance with an associated therapeutic regimen for a particular therapeutic will be much higher than compliance is presently for the same or similar therapeutic in injectable form.

The ingestible device includes one or more shaped compositions (e.g., the shaped composition 160) and a delivery mechanism (e.g., the delivery mechanism 102) including an expandable enclosure having a head region, a tail region, and at least one retention region between the head region and the tail region (e.g., the expandable enclosure 120 including the head region 122, the tail region 124, and the retention region 130). The shaped composition is disposed adjacent to the retention region and may be affixed to the retention region. The shaped composition includes one or more therapeutic agents (e.g., the therapeutic agent 862) and/or one or more delivery enhancing agents (e.g., the delivery enhancing agent 864).

The ingestible device remains substantially intact by design during traversal through the GI tract to a delivery location (e.g., a target delivery location). In one or more embodiments, the target delivery location is within the small intestine. In one or more embodiments, the target delivery location is within the jejunum; in such embodiments, the ingestible device remains substantially intact by design until entering the small intestine, where after a designed delay for the ingestible device to reach the jejunum portion of the small intestine, the ingestible device releases the shaped composition into the jejunum as follows at 1410, 1420, and 1430.

At 1410, a structure of the ingestible device of the associated therapeutic regimen provides for expansion of the expandable enclosure at the target delivery location. In one or more embodiments, the expandable enclosure is structured to be expandable by an expansion mechanism responsive to a condition in the GI tract. For example, the condition in the GI tract can include a pH in the small intestine (e.g., pH<7, or a pH in a range from 6.5 to 7.5). In one or more embodiments, the expansion mechanism is a chemical reaction between two or more chemicals disposed in the expandable enclosure when the chemicals are allowed to mix by release of a barrier (e.g., the separation barrier 140) separating the chemicals.

As the expandable enclosure expands, the head region and the tail region expand to contact a surface at the delivery location (e.g., an inner wall of the small intestine) to minimize or prevent a flow of digestive matter into a protective recess formed between the head region and the tail region, to facilitate release and effectiveness of the shaped composition(s).

In one or more embodiments, a degradable coating (e.g., the degradable coating 866, 867, 868, 869, or 896) of the shaped composition is structured to degrade and hence deliver the therapeutic agent a designed period of time (e.g., 1 minute, 5 minutes, etc.) after the shaped composition is exposed to digestive matter at the target delivery location, such as when an outer shell (e.g., the outer shell 110) of the ingestible device sufficiently degrades to allow digestive matter to breach the outer shell. Such delay can allow expansion of the expandable enclosure to be completed and the protective recess to be formed by the expandable enclosure prior to the therapeutic agent and/or the delivery enhancing agent being released from the shaped composition to the delivery location.

At 1420, the delivery enhancing agent is released into the protective recess, where it can remain to enhance the transport of the therapeutic agent, as discussed above.

At 1430, the therapeutic agent is released into the protective recess, where it can remain until transport across the intestinal wall.

The shaped composition can be structured to release the delivery enhancing agent prior to, concurrently with, or after delivery of the therapeutic agent. Further, a sequence of release can be designed (e.g., as discussed with respect to FIGS. 8A-8E) to effectuate any desired order of release of multiple therapeutic agents and/or multiple delivery enhancing agents. For example, the shaped composition can be designed to release a first delivery enhancing agent prior to release of a first therapeutic agent, and to release a second delivery enhancing agent subsequent to release of the first therapeutic agent or a second therapeutic agent. For another example, the shaped composition can be designed to release a first dose of a therapeutic agent, and, after a delay, to release a second dose of the same or a similar therapeutic agent. For a further example, the shaped composition can be designed to release a first therapeutic agent, and after a delay, to release a second therapeutic agent different than the first therapeutic agent. In one or more embodiments, multiple shaped compositions can be incorporated into the ingestible device to deliver higher dosages of a therapeutic agent and/or a delivery enhancing agent than may be possible with a single ingestible device, or to deliver different therapeutics, or to achieve a particular sequencing of releases of therapeutic agents and delivery enhancing agents.

In an aspect, embodiments provide for an ingestible device for delivery of a therapeutic formulation, which ingestible device includes a swallowable outer shell and a delivery mechanism within the outer shell. The delivery mechanism includes an expandable enclosure. The delivery mechanism is triggerable in situ within a GI tract of a body to expand multiple regions of the expandable enclosure at a delivery location within the body. The multiple regions of the expandable enclosure include a head region and a tail region together defining a protective recess between the head region and the tail region, and a retention region within the protective recess. A dimension of the retention region as expanded is less than a dimension of the head region as expanded and less than a dimension of the tail region as expanded. The ingestible device includes a shaped composition disposed at the retention region.

In an aspect, embodiments provide for a method for delivery of a therapeutic agent into an intestine (or other portion of a GI tract) of a subject using an ingestible device. The ingestible device includes a shaped composition and a delivery mechanism. The delivery mechanism includes an expandable enclosure with a head region and a tail region. The shaped composition includes the therapeutic agent and a delivery enhancing agent selected to enhance transport of the therapeutic agent across a wall of the intestine. The method further includes instructing or causing the subject to ingest the ingestible device and thereby initiate traversal of the ingestible device through the intestine and subsequently initiate transport of the agent(s) through the wall of the intestine. Initiation of the transport is achieved by the delivery mechanism being structured to expand the expandable enclosure responsive to a condition in the intestine, such that a head region and a tail region of the expandable enclosure expand against the wall of the intestine to define a protective recess bounded in situ by the wall of the intestine. The shaped composition is disposed within the protective recess and therein exposed to the intestine. The exposure of the shaped composition to the intestine initiates release of the delivery enhancing agent from the shaped composition into the protective recess to enhance the transport of the therapeutic agent through the wall of the intestine. The exposure of the shaped composition to the intestine also initiates release of the therapeutic agent into the protective recess for transport through the wall of the intestine.

In an aspect, embodiments provide for a method for providing a shaped composition including a therapeutic agent. The method includes structuring a delivery mechanism triggerable within a selected portion of the GI tract to expand each of a head region of an expandable enclosure and a tail region of the expandable enclosure to a fully expanded state. The expandable enclosure includes a retention region that is structured to be expanded in situ to a dimension less than a corresponding dimension of the head region and less than a corresponding dimension of the tail region. The method further includes attaching a shaped composition to the retention region and placing the expandable enclosure within a shell.

In an aspect, embodiments provide for a method for oral delivery of a therapeutic agent to a subject. The method includes ingesting an ingestible device including a shaped composition and a delivery mechanism, and providing for transport of the therapeutic agent across an intestinal wall. The delivery mechanism includes an expandable enclosure having head and tail regions. The shaped composition includes the therapeutic agent and a delivery enhancing agent to enhance the transport of the therapeutic agent across the intestinal wall. Transport of the therapeutic agent across the intestinal wall is provided for by: expanding the head and tail regions responsive to a condition in the small intestine, such that the head and tail regions expand against the intestinal wall to form a sealed section of intestine for delivery of the therapeutic agent; releasing the delivery enhancing agent into the sealed intestinal section where it remains to enhance the transport of the therapeutic agent; and releasing the therapeutic agent into the sealed intestinal section, where it remains until transport of the therapeutic agent across the intestinal wall.

In an aspect, embodiments provide for a method for the oral delivery of a therapeutic agent to a patient, the therapeutic agent degraded by secretions of the GI tract, where the method includes swallowing an ingestible device containing a shaped composition and further containing an expandable enclosure having head and tail regions, the shaped composition including the therapeutic agent and a delivery enhancing agent structured to enhance transport of the therapeutic agent across an intestinal wall. The method further includes: expanding the head and tail regions responsive to a condition in the intestine, such that the head and tail regions form a sealed section of intestine for delivery of the therapeutic agent; releasing the delivery enhancing agent into the sealed intestinal section where it remains to enhance the transport of the therapeutic agent; releasing the therapeutic agent into the sealed intestinal section where it remains until transport across the intestinal wall; and transporting the therapeutic agent across the intestinal wall in the sealed section of intestine, where transport is enhanced by the delivery enhancing agent.

In any of the foregoing aspects, a swallowable outer shell can be structured to degrade in situ in a presence of digestive matter at a target delivery location, or during traversal through the body to the target delivery location.

In any of the foregoing aspects, a swallowable outer shell can be structured to withstand degradation within a stomach of the body, or to degrade over a time period that exceeds a time of traversal of the ingestible device into and through the stomach.

In any of the foregoing aspects, a swallowable outer shell can be structured to degrade at a pH in a range between 6.5 and 7.5, or at a pH greater than 7.

In any of the foregoing aspects, the ingestible device can include a degradable coating encasing the shaped composition, and the degradable coating can be structured for resilience to digestive matter present at a target delivery location for at least a designed period of time.

In any of the foregoing aspects, an ingestible device can include at least one expansion mechanism disposed within an expandable enclosure.

In any of the foregoing aspects, an ingestible device can include a separation barrier, where an expansion mechanism includes a first chemical reactant and a second chemical reactant, and the first chemical reactant is separated from the second chemical reactant by the separation barrier, and where the first chemical reactant and the second chemical reactant are reactive to each other to generate a gas to expand an expandable enclosure. The separation barrier can be structured to degrade in situ upon exposure to digestive matter, subsequent to a degradation of a swallowable outer shell sufficient to allow the digestive matter to breach an interior region of the swallowable outer shell. The first chemical reactant can include potassium bicarbonate, and the second chemical reactant can include citric acid. The ingestible device can further include a seal that closes off an opening in the expandable enclosure, where the seal can be structured to degrade in situ upon exposure to digestive matter subsequent to a degradation of the swallowable outer shell sufficient to allow the digestive matter to breach an interior region of the swallowable outer shell, and where a rate of degradation of the seal is designed to be slower than a rate of degradation of the separation barrier.

In any of the foregoing aspects, an expandable enclosure can be structured for less expansion at a retention region as compared to expansion of a head region or expansion of a tail region.

In any of the foregoing aspects, in an expanded state of an expandable enclosure, a head region, a tail region, and at least one mid-region together can define multiple protective recesses. The ingestible device can include multiple shaped compositions disposed in one or more of the protective recesses. Each of the multiple shaped compositions can include one or more agents. At least one of the multiple shaped compositions can include a different combination or a different volume or mass of agents than another of the multiple shaped compositions. Each agent of the multiple shaped compositions can be one of a drug, an excipient, or a delivery enhancing agent.

In any of the foregoing aspects, an ingestible device can operate to deliver a formulation in response to a condition. The condition can be a pH in a small intestine. For example, the pH can be in a range from about 6.5 to 7.5.

In any of the foregoing aspects, a delivery enhancing agent can include a protease inhibitor.

In any of the foregoing aspects, a delivery enhancing agent can include a permeability enhancer which enhances a permeability of a wall of a small intestine to a therapeutic agent.

In any of the foregoing aspects, a delivery enhancing agent can fluidize a plasma membrane of cells in an epithelial layer of the small intestine.

In any of the foregoing aspects, a permeability enhancer can include an MCFA-based sodium caprate, sodium caprylate, sodium caprylate derivative, acyl carnitines or EDTA.

In any of the foregoing aspects, a delivery enhancing agent can induce sloughing of cells from an epithelial layer of an intestinal wall.

In any of the foregoing aspects, a shaped composition can include a coating which is structured to degrade in a small intestine after a designed period of time, such that a delivery enhancing agent and a therapeutic agent are released into a protective recess of an expandable enclosure after the designed period of time. The designed period of time can be greater than a designed time for expansion of a head region and a tail region of the expandable enclosure.

In any of the foregoing aspects, an initiation of release of a therapeutic agent is subsequent to an initiation of release of a delivery enhancing agent.

In any of the foregoing aspects, a delivery mechanism expands a head region and a tail region by a chemical reaction.

In any of the foregoing aspects, multiple shaped compositions can be disposed in an ingestible device, and a mass of a therapeutic agent in a first shaped composition is a first mass. At least a second one of the shaped compositions can include a different mass of the therapeutic agent than the first mass. The shaped compositions can include at least the first therapeutic agent and a second therapeutic agent different than the first therapeutic agent. The shaped compositions can include a second shaped composition including the therapeutic agent, where the first shaped composition can be designed to release the therapeutic agent after a first time period subsequent to the exposure to the intestine, the second shaped composition can be designed to release the therapeutic agent after a second time period subsequent to the exposure to the intestine, and the second time period can be designed to be longer than the first time period. The shaped compositions can include one or more delivery enhancing agents.

In any of the foregoing aspects, an ingestible device can include an enteric coating structured to withstand degradation when exposed to contents in a stomach, and the enteric coating can be structured to degrade in the intestine.

In any of the foregoing aspects, a shaped composition can include a disintegrant or a superdisintegrant.

In any of the foregoing aspects, a therapeutic agent can include an immunoglobulin. The immunoglobulin can be immunoglobulin G. The immunoglobulin can be a TNF-alfa antibody. The TNF-alfa antibody can be adalimumab. The immunoglobulin can be an antibody to an interleukin in an IL-17 family of interleukins (AI17 antibody). the AI17 antibody can be brodalumab, secukinumab or ixekizumab.

In any of the foregoing aspects, the shaped composition can be one of multiple shaped compositions disposed at the retention region In any of the foregoing aspects, the shaped composition can be structured to define an opening extending through the shaped composition, and the expandable enclosure can be disposed through the opening such that portions of the expandable enclosure extend on either side of the opening. In such embodiments, the shaped composition can restrict expansion of the expandable enclosure; or, the expandable enclosure is structured for minimal expansion along a length of the expandable enclosure defining the retention region, and the shaped composition is positioned along the length; in either case, a constricting structure or other technique (e.g., increasing a material thickness of a portion of the expandable enclosure) may be additionally incorporated for limiting expansion of the expandable enclosure.

CONCLUSION

As can be seen from the illustrations and descriptions herein, embodiments of an ingestible device can provide for a variety of formulation delivery options. In one or more embodiments, for example, up to twenty milligrams of therapeutic formulation may be delivered by an ingestible device in accordance with the concepts of the present disclosure. In other embodiments, more than twenty milligrams of therapeutic formulation may be delivered by an ingestible device in accordance with the concepts of the present disclosure. In one or more embodiments, a percentage of the therapeutic formulation present in the shaped composition is delivered effectively, and the remainder of the therapeutic formulation is expelled from the body. Thus, a design of the type and number of shaped compositions to be used in an ingestible device may be increased to account for the effective delivery. For example, if twenty milligrams of therapeutic formulation is desired to be effectively delivered, the ingestible device may be designed to provide one hundred to two hundred milligrams of the therapeutic formulation to the GI tract, depending on the expected absorption rate through a wall of the GI tract into a vascularized area of the body.

As used herein, the terms "substantially" and "about" are used to describe and account for small variations. For example, when used in conjunction with a numerical value, the terms can refer to a variation in the value of less than or equal to ±10%, such as less than or equal to ±5%, less than or equal to ±4%, less than or equal to ±3%, less than or equal to ±2%, less than or equal to ±1%, less than or equal to ±0.5%, less than or equal to ±0.1%, or less than or equal to ±0.05%.

As used herein, a range of numbers includes any number within the range, or any sub-range if the minimum and maximum numbers in the sub-range fall within the range. Thus, for example, "<9" can refer to any number less than nine, or any sub-range of numbers where the minimum of the sub-range is greater than or equal to zero and the maximum of the sub-range is less than nine.

While the present disclosure has been described and illustrated with reference to specific embodiments thereof, these descriptions and illustrations do not limit the present disclosure. It can be clearly understood that various changes may be made, and equivalent components may be substituted within the embodiments without departing from the true spirit and scope of the present disclosure as defined by the appended claims. Also, elements, characteristics, or acts from one embodiment can be readily recombined or substituted with one or more elements, characteristics or acts from other embodiments to form numerous additional embodiments within the scope of the invention. Moreover, elements that are shown or described as being combined with other elements, can, in various embodiments, exist as standalone elements. Further, for any positive recitation of an element, characteristic, constituent, feature, step or the like, embodiments of the invention specifically contemplate the exclusion of that element, value, characteristic, constituent, feature, step or the like. The illustrations may not necessarily be drawn to scale. There may be distinctions between the artistic renditions in the present disclosure and the actual apparatus, due to variables in manufacturing processes and such. There may be other embodiments of the present disclosure which are not specifically illustrated. The specification and drawings are to be regarded as illustrative rather than restrictive. Modifications may be made to adapt a particular situation, material, composition of matter, method, or process to the objective, spirit and scope of the present disclosure. All such modifications are intended to be within the scope of the claims appended hereto. While the methods disclosed herein have been described with reference to particular operations performed in a particular order, it can be understood that these operations may be combined, sub-divided, or re-ordered to form an equivalent method without departing from the teachings of the present disclosure. Therefore, unless specifically indicated herein, the order and grouping of the operations are not limitations of the present disclosure.

The invention claimed is:

1. A method for delivering a therapeutic agent into a small intestine of a subject using an ingestible device, the method comprising:
   administering the ingestible device to the subject by ingestion and thereby initiating transport of the device to the small intestine, wherein the ingestible device comprises an outer shell that contains (i) a shaped composition comprising the therapeutic agent and (ii) a delivery mechanism, the delivery mechanism comprising an expandable enclosure including a head region, a predetermined retention region, and a tail region, wherein the expandable enclosure is structured such that, when expanded, a dimension of the predetermined retention region of the expanded expandable enclosure is less than a dimension of the head region of the expanded expandable enclosure and less than a dimension of the tail region of the expanded expandable enclosure, wherein the delivery mechanism is structured to expand the expandable enclosure responsive to a condition in the small intestine;
   wherein the outer shell degrades in situ in the small intestine to expose the delivery mechanism, wherein responsive to said condition in the small intestine, the delivery mechanism expands the expandable enclosure such that the head region and the tail region of the expandable enclosure expand against a wall of the small intestine, wherein a dimension of the predetermined retention region of the expanded expandable enclosure is less than a dimension of the head region of the expanded expandable enclosure and less than a dimension of the tail region of the expanded expandable enclosure, to define a protective volume bounded by the expanded expandable enclosure and the wall of the small intestine, wherein the shaped composition is disposed within the protective volume and exposed to the small intestine; and
   wherein exposure of the shaped composition to the small intestine initiates degradation of the shaped composition that releases the therapeutic agent from the shaped composition into the protective volume for transport through the wall of the small intestine.

2. The method of claim 1, wherein the condition in the small intestine is a pH in the small intestine.

3. The method of claim 1, wherein the shaped composition comprises a coating which is structured to degrade in the small intestine after a designed period of time, such that the therapeutic agent is released into the protective volume after the designed period of time.

4. The method of claim 3, wherein the designed period of time is greater than a designed time for expansion of the head region and the tail region of the expandable enclosure.

5. The method of claim 1, wherein the shaped composition further comprises a delivery enhancing agent selected to enhance transport of the therapeutic agent across the wall of the small intestine, wherein exposure of the shaped composition to the small intestine initiates degradation of the shaped composition that releases the delivery enhancing agent from the shaped composition into the protective volume to enhance transport of the therapeutic agent through the wall of the small intestine, and wherein the initiation of the release of the therapeutic agent is subsequent to the initiation of the release of the delivery enhancing agent.

6. The method of claim 1, wherein the delivery mechanism expands the head region and the tail region by a chemical reaction.

7. The method of claim 1, wherein the shaped composition is a first shaped composition of a plurality of shaped compositions disposed in the ingestible device, and a mass of the therapeutic agent in the first shaped composition is a first mass.

8. The method of claim 7, wherein at least a second one of the plurality of shaped compositions comprises a different mass of the therapeutic agent than the first mass.

9. The method of claim 7, wherein the therapeutic agent is a first therapeutic agent and the plurality of shaped compositions comprises at least the first therapeutic agent and a second therapeutic agent different than the first therapeutic agent.

10. The method of claim 7, wherein the plurality of shaped compositions comprises a second shaped composition comprising the therapeutic agent, the first shaped composition is designed to release the therapeutic agent after a first time period subsequent to the exposure to the small intestine, the second shaped composition is designed to release the therapeutic agent after a second time period subsequent to the exposure to the small intestine, and the second time period is designed to be longer than the first time period.

11. The method of claim 7, wherein the plurality of shaped compositions comprises at least a first delivery enhancing agent and a second delivery enhancing agent different than the first delivery enhancing agent, wherein the first and second delivery enhancing agents are selected to enhance transport of the therapeutic agent across the wall of the small intestine.

12. The method of claim 1, wherein the therapeutic agent comprises an immunoglobulin.

13. The method of claim 12, wherein the immunoglobulin comprises immunoglobulin G.

14. The method of claim 12, wherein the immunoglobulin comprises a TNF-alpha antibody.

15. The method of claim 12, wherein the immunoglobulin comprises an antibody to an interleukin in an IL-17 family of interleukins.

16. The method of claim 1, wherein the shaped composition further comprises a delivery enhancing agent selected to enhance transport of the therapeutic agent across the wall of the small intestine.

17. The method of claim 16, wherein the delivery enhancing agent comprises a protease inhibitor.

18. The method of claim 16, wherein the delivery enhancing agent comprises a permeability enhancer which enhances a permeability of a wall of the small intestine to the therapeutic agent.

19. The method of claim 18, wherein the delivery enhancing agent fluidizes a plasma membrane of cells in an epithelial layer of the small intestine.

20. The method of claim 19, wherein the permeability enhancer comprises a medium chain fatty acid (MCFA)-based sodium caprate, sodium caprylate, sodium caprylate derivative, acyl carnitines or ethylenediaminetetraacetic acid (EDTA).

21. The method of claim 18, wherein the delivery enhancing agent induces sloughing of cells from an epithelial layer of an intestinal wall.

* * * * *